United States Patent
Koehn et al.

(10) Patent No.: US 9,732,048 B2
(45) Date of Patent: Aug. 15, 2017

(54) N-(ISOXAZOL-3-YL)-ARYL-CARBOXYLIC ACID AMIDES AND USE THEREOF AS HERBICIDES

(71) Applicant: BAYER CROPSCIENCE AG, Monheim (DE)

(72) Inventors: Arnim Koehn, Klein-Winternheim (DE); Hartmut Ahrens, Egelsbach (DE); Ralf Braun, Ramberg (DE); Ines Heinemann, Hofheim (DE); Joerg Tiebes, Frankfurt (DE); Christian Waldraff, Bad Vilbel (DE); Hansjoerg Dietrich, Liederbach am Taunus (DE); Elmar Gatzweiler, Bad Nauheim (DE); Christopher Hugh Rosinger, Hofheim am Taunus (DE); Dirk Schmutzler, Hattersheim (DE)

(73) Assignee: BAYER CROPSCIENCE AG, Monheim (DE)

( * ) Notice: Subject to any disclaimer, the term of this patent is extended or adjusted under 35 U.S.C. 154(b) by 0 days.

(21) Appl. No.: 14/648,032

(22) PCT Filed: Dec. 3, 2013

(86) PCT No.: PCT/EP2013/075317
§ 371 (c)(1),
(2) Date: May 28, 2015

(87) PCT Pub. No.: WO2014/086746
PCT Pub. Date: Jun. 12, 2014

(65) Prior Publication Data
US 2015/0307462 A1    Oct. 29, 2015

(30) Foreign Application Priority Data
Dec. 7, 2012  (EP) ..................... 12195981

(51) Int. Cl.
C07D 261/14   (2006.01)
C07D 413/12   (2006.01)
A01N 43/80    (2006.01)

(52) U.S. Cl.
CPC ........... C07D 261/14 (2013.01); A01N 43/80 (2013.01); C07D 413/12 (2013.01)

(58) Field of Classification Search
CPC .................................................. C07D 261/14
USPC .......................................... 548/246; 504/271
See application file for complete search history.

(56) References Cited

U.S. PATENT DOCUMENTS

| 4,416,683 A | 11/1983 | Burow |
| 2009/0163545 A1* | 6/2009 | Goldfarb .............. A61K 31/122 514/312 |

FOREIGN PATENT DOCUMENTS

| GB | 2126227 A | 3/1984 |
| JP | 649978 B2 | 2/1989 |

OTHER PUBLICATIONS

International Search Report from corresponding PCT/EP2013/075317, mailed Jan. 31, 2014.
Database WPI, Aug. 1989, Thomson Scientific, London, GB, XP002693638, 1 page.
Database Registry, Chemical Abstracts Service, Columbus, Ohio, Nov. 30, 2012, XP002693639.

* cited by examiner

*Primary Examiner* — Patricia L Morris
(74) *Attorney, Agent, or Firm* — McBee Moore Woodward Vanik IP; Susan McBee; David Woodward

(57) ABSTRACT

The invention relates to N-(isoxazol-3-yl)-aryl-carboxylic acid amides and use thereof as herbicides. In formula (I), A stands for N or C—Y. R, V, X, Y, and Z stand for groups such as hydrogen, halogen, and organic groups such as substituted alkyl.

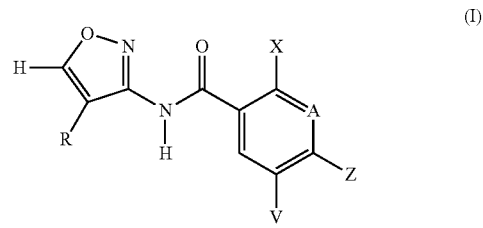

12 Claims, No Drawings

N-(ISOXAZOL-3-YL)-ARYL-CARBOXYLIC ACID AMIDES AND USE THEREOF AS HERBICIDES

CROSS REFERENCE TO RELATED APPLICATIONS

This application is a §371 National Stage Application of PCT/EP2013/075317, filed 3 Dec. 2013, which claims priority to EP 12195981.1, filed 7 Dec. 2012.

BACKGROUND

Field of the Invention

The invention relates to the technical field of the herbicides, especially that of the herbicides for selective control of broad-leaved weeds and weed grasses in crops of useful plants.

Description of Related Art

WO 2011/035874 A1 discloses N-(1,2,5-oxadiazol-3-yl)benzamides and use thereof as herbicides. WO 2012/028579 A1 discloses N-(tetrazol-5-yl)- and N-(triazol-5-yl)arylcarboxamides and their use as herbicides. Perfluoroalkylisoxazole derivatives and their use as herbicides are known from JP 01009978 A.

Under the following CAS numbers, the compounds which are mentioned following each one are known:

1283281-40-2: 4,5-difluoro-2-nitro-N-(1,2-oxazol-3-yl)benzamide, 1275071-21-0: 2-bromo-4-fluoro-N-(1,2-oxazol-3-yl)benzamide, 950245-82-6: 2,4-dichloro-N-(1,2-oxazol-3-yl)benzamide, 932855-85-1: 2,4-dimethoxy-N-(1,2-oxazol-3-yl)benzamide, 886633-07-4: 2,4-diethoxy-N-(1,2-oxazol-3-yl)benzamide, 886630-79-1: 2-chloro-4-fluoro-N-(1,2-oxazol-3-yl)benzamide, 830341-63-4: 2-chloro-4,5-difluoro-N-(1,2-oxazol-3-yl)benzamide, 587852-24-2: 2,4,5-trimethoxy-N-(1,2-oxazol-3-yl)benzamide, and 1408387-94-9: 4-bromo-4-fluoro-N-(1,2-oxazol-3-yl)benzamide.

No herbicidal effect of the compounds known by their CAS numbers has been disclosed. US20090163545 A1 describes a pharmacological activity of the compound 2-methoxy-4-(methylsulfanyl)-N-(1,2-oxazol-3-yl)benzamide.

However, the compounds known from these documents exhibit zero or frequently inadequate herbicidal efficacy. It is an object of the present invention to provide further herbicidally active compounds.

It has now been found that N-(isoxazol-3-yl)-arylcarboxamides which carry hydrogen in the 5-position of the isoxazole ring and certain substituents in the 4-position of the isoxazole ring and in the arylcarboxylic acid moiety are particularly suitable for use as herbicides.

SUMMARY

Accordingly, the present invention provides N-(isoxazol-3-yl)arylcarboxamides of the formula (I) or salts thereof

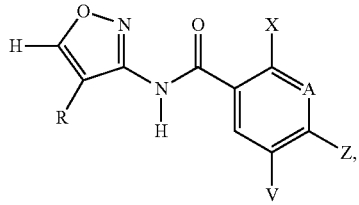

in which

A represents N or CY,

R represents hydrogen, $(C_1-C_6)$-alkyl, $(C_3-C_7)$-cycloalkyl, halo-$(C_1-C_6)$-alkyl, $(C_1-C_6)$-alkoxy, halo-$(C_1-C_6)$-alkoxy, $(C_2-C_6)$-alkenyl, $(C_2-C_6)$-alkenyloxy, $(C_2-C_6)$-haloalkenyl, $(C_2-C_6)$-alkynyl, $(C_2-C_6)$-alkynyloxy, $(C_2-C_6)$-haloalkynyl, cyano-$(C_1-C_6)$-alkyl, cyano, nitro, methylsulfenyl, methylsulfinyl, methylsulfonyl, acetylamino, benzoylamino, methoxycarbonyl, ethoxycarbonyl, methoxycarbonylmethyl, ethoxycarbonylmethyl, benzoyl, methylcarbonyl, piperidinylcarbonyl, trifluoromethylcarbonyl, halogen, amino, aminocarbonyl, methylaminocarbonyl, dimethylaminocarbonyl, methoxymethyl, or heteroaryl, heterocyclyl or phenyl, each of which is substituted by s radicals from the group consisting of methyl, ethyl, methoxy, trifluoromethyl and halogen, X represents nitro, halogen, cyano, formyl, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $C(O)NR^1OR^1$, $OR^2$, $OCOR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $NR_1R_2$, $P(O)(OR^5)_2$, $CH_2P(O)(OR^5)_2$, $(C_1-C_6)$-alkyl-heteroaryl, $(C_1-C_6)$-alkyl-heterocyclyl, where the two last-mentioned radicals are each substituted by s radicals from the group consisting of halogen, $(C_1-C_6)$-alkyl, halo-$(C_1-C_6)$-alkyl, $S(O)_n$—$(C_1-C_6)$-alkyl, $(C_1-C_6)$-alkoxy and halo-$(C_1-C_6)$-alkoxy, and where heterocyclyl carries n oxo groups, Y represents hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $CO(NOR^1)R^1$, $CHNOR^1$, $CH_2ONCR^3)_2$, $NR^1SO_2R^2$, $NR^1COR^1$, $OR^1$, $OSO_2R^2$, $S(O)_nR^2$, $SO_2OR^1$, $SO_2N(R^1)_2$ $(C_1-C_6)$-alkyl-$S(O)_nR^2$, $NS(O)R^8R^7$, $S(O)R^8NR^9$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-CN, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $N(R^1)_2$, $P(O)(OR^5)_2$, $CH_2P(O)(OR^5)_2$, $(C_1-C_6)$-alkylphenyl, $(C_1-C_6)$-alkylheteroaryl, $(C_1-C_6)$-alkylheterocyclyl, phenyl, heteroaryl or heterocyclyl, where the 6 last-mentioned radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-$ $C_6$)-alkoxy, halo-($C_1$-$C_6$)-alkoxy, ($C_1$-$C_6$)-alkoxy-($C_1$-$C_4$)-alkyl and cyanomethyl, and where heterocyclyl carries 0 to 2 oxo groups, Z represents halogen, cyano, thiocyanato, nitro, ($C_1$-$C_6$)-alkyl, ($C_1$-$C_6$)-alkoxy, halo-($C_1$-$C_6$)-alkyl, ($C_2$-$C_6$)-alkenyl, halo-($C_2$-$C_6$)-alkenyl, ($C_2$-$C_6$)-alkynyl, halo-($C_2$-$C_6$)-alkynyl, ($C_3$-$C_6$)-cycloalkyl, halo-($C_3$-$C_6$)-cycloalkyl, ($C_3$-$C_6$)-cycloalkyl-($C_1$-$C_6$)-alkyl, halo-($C_3$-$C_6$)-cycloalkyl-($C_1$-$C_6$)-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $C(O)NR^1OR^1$, $OSO_2R^2$, $S(O)_nR^2$, $SO_2OR^1$, $SO_2N(R^1)_2$, $NR^1SO_2R^2$, $NR^1COR^1$, ($C_1$-$C_6$)-alkyl-$S(O)_nR^2$, ($C_1$-$C_6$)-alkyl-$OR^1$, ($C_1$-$C_6$)-alkyl-$OCOR^1$, ($C_1$-$C_6$)-alkyl-$OSO_2R^2$, ($C_1$-$C_6$)-alkyl-$SO_2R^1$, ($C_1$-$C_6$)-alkyl-$SO_2OR^1$, ($C_1$-$C_6$)-alkyl-$CON(R^1)_2$, ($C_1$-$C_6$)-alkyl-$SO_2N(R^1)_2$, ($C_1$-$C_6$)-alkyl-$NR^1COR^1$, ($C_1$-$C_6$)-alkyl-$NR^1SO_2R^2$, $NR^1R^2$, $P(O)(OR^5)_2$, heteroaryl, heterocyclyl or phenyl, where the three last-mentioned radicals are each substituted by s radicals from the group consisting of halogen, nitro, cyano, ($C_1$-$C_6$)-alkyl, halo-($C_1$-$C_6$)-alkyl, ($C_3$-$C_6$)-cycloalkyl, $S(O)_n$—($C_1$-$C_6$)-alkyl, ($C_1$-$C_6$)-alkoxy or halo-($C_1$-$C_6$)-alkoxy, and where heterocyclyl carries 0 to 2 oxo groups, or Z may also represent hydrogen if Y represents the $S(O)_nR^2$ radical, V represents hydrogen, ($C_1$-$C_6$)-alkyl, halo-($C_1$-$C_6$)-alkyl, ($C_1$-$C_6$)-alkoxy, ($C_1$-$C_6$)-haloalkoxy, $S(O)_n$—($C_1$-$C_6$)-alkyl, $S(O)_n$—($C_1$-$C_6$)-haloalkyl, ($C_1$-$C_6$)-alkoxy-($C_1$-$C_4$)-alkyl, halogen, nitro or cyano, $R^1$ represents hydrogen, ($C_1$-$C_6$)-alkyl, ($C_1$-$C_6$)-haloalkyl, ($C_2$-$C_6$)-alkenyl, ($C_2$-$C_6$)-haloalkenyl, ($C_2$-$C_6$)-alkynyl, ($C_2$-$C_6$)-haloalkynyl, ($C_3$-$C_6$)-cycloalkyl, ($C_3$-$C_6$)-cycloalkenyl, ($C_3$-$C_6$)-halocycloalkyl, ($C_1$-$C_6$)-alkyl-O—($C_1$-$C_6$)-alkyl, ($C_3$-$C_6$)-cycloalkyl-($C_1$-$C_6$)-alkyl, phenyl, phenyl-($C_1$-$C_6$)-alkyl, heteroaryl, ($C_1$-$C_6$)-alkylheteroaryl, heterocyclyl, ($C_1$-$C_6$)-alkylheterocyclyl, ($C_1$-$C_6$)-alkyl-O-heteroaryl, ($C_1$-$C_6$)-alkyl-O-heterocyclyl, ($C_1$-$C_6$)-alkyl-$NR^3$-heteroaryl, ($C_1$-$C_6$)-alkyl-$NR^3$-heterocyclyl, where the 21 last-mentioned radicals are substituted by s radicals from the group consisting of cyano, halogen, nitro, thiocyanato, $OR^3$, $S(O)_nR^4$, $N(R^3)_2$, $NR^3OR^3$, $COR^3$, $OCOR^3$, $SCOR^4$, $NR^3COR^3$, $NR^3SO_2R^4$, $CO_2R^3$, $COSR^4$, $CON(R^3)_2$ and ($C_1$-$C_4$)-alkoxy-($C_2$-$C_6$)-alkoxycarbonyl, and where heterocyclyl carries 0 to 2 oxo groups, $R^2$ represents ($C_1$-$C_6$)-alkyl, ($C_1$-$C_6$)-haloalkyl, ($C_2$-$C_6$)-alkenyl, ($C_2$-$C_6$)-haloalkenyl, ($C_2$-$C_6$)-alkynyl, ($C_2$-$C_6$)-haloalkynyl, ($C_3$-$C_6$)-cycloalkyl, ($C_3$-$C_6$)-cycloalkenyl, ($C_3$-$C_6$)-halocycloalkyl, ($C_1$-$C_6$)-alkyl-O—($C_1$-$C_6$)-alkyl, ($C_3$-$C_6$)-cycloalkyl-($C_1$-$C_6$)-alkyl, phenyl, phenyl-($C_1$-$C_6$)-alkyl, heteroaryl, ($C_1$-$C_6$)-alkylheteroaryl, heterocyclyl, ($C_1$-$C_6$)-alkylheterocyclyl, ($C_1$-$C_6$)-alkyl-O-heteroaryl, ($C_1$-$C_6$)-alkyl-O-heterocyclyl, ($C_1$-$C_6$)-alkyl-$NR^3$-heteroaryl, ($C_1$-$C_6$)-alkyl-$NR^3$-heterocyclyl, where the 21 last-mentioned radicals are substituted by s radicals from the group consisting of cyano, halogen, nitro, thiocyanato, $OR^3$, $S(O)_nR^4$, $N(R^3)_2$, $NR^3OR^3$, $COR^3$, $OCOR^3$, SCOW, $NR^3COR^3$, $NR^3SO_2R^4$, $CO_2R^3$, $COSR^4$, $CON(R^3)_2$ and ($C_1$-$C_4$)-alkoxy-($C_2$-$C_6$)-alkoxycarbonyl, and where heterocyclyl carries 0 to 2 oxo groups, $R^3$ represents hydrogen, ($C_1$-$C_6$)-alkyl, ($C_2$-$C_6$)-alkenyl, ($C_2$-$C_6$)-alkynyl, ($C_3$-$C_6$)-cycloalkyl or ($C_3$-$C_6$)-cycloalkyl-($C_1$-$C_6$)-alkyl, $R^4$ represents ($C_1$-$C_6$)-alkyl, ($C_2$-$C_6$)-alkenyl or ($C_2$-$C_6$)-alkynyl, ($C_3$-$C_6$)-cycloalkyl, ($C_3$-$C_6$)-cycloalkyl-($C_1$-$C_6$)-alkyl or phenyl, $R^5$ represents methyl or ethyl, $R^6$ and $R^7$ independently of one another each represent ($C_1$-$C_6$)-alkyl, halo-($C_1$-$C_6$)-alkyl, ($C_2$-$C_6$)-alkenyl, halo-($C_2$-$C_6$)-alkenyl, ($C_2$-$C_6$)-alkynyl, halo-($C_3$-$C_6$)-alkynyl, ($C_3$-$C_6$)-cycloalkyl, halo-($C_3$-$C_6$)-cycloalkyl, ($C_3$-$C_6$)-cycloalkyl-($C_1$-$C_6$)-alkyl, halo-($C_3$-$C_6$)-cycloalkyl-($C_1$-$C_6$)-alkyl, ($C_1$-$C_6$)-alkoxy-($C_1$-$C_6$)-alkyl, halo-($C_1$-$C_6$)-alkoxy-($C_1$-$C_6$)-alkyl, phenyl, heteroaryl or heterocyclyl, where the three last-mentioned radicals are each substituted by s radicals from the group consisting of nitro, halogen, cyano, thiocyanato, ($C_1$-$C_6$)-alkyl, halo-($C_1$-$C_6$)-alkyl, ($C_3$-$C_6$)-cycloalkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O$—($C_1$-$C_6$)-alkyl, and where heterocyclyl carries n oxo groups, or $R^6$ and $R^7$ together with the sulfur atom to which they are attached form a 3- to 8-membered unsaturated, partly saturated or saturated ring which contains, apart from the carbon atoms and apart from the sulfur atom of the sulfoximino group, in each case m ring members from the group consisting of $N(R^1)$, O and $S(O)_n$, and where this ring is in each case substituted by s radicals from the group consisting of nitro, halogen, cyano, thiocyanato, ($C_1$-$C_6$)-alkyl, halo-($C_1$-$C_6$)-alkyl, ($C_3$-$C_6$)-cycloalkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O$—($C_1$-$C_6$)-alkyl, and where this ring carries n oxo groups, $R^8$ represents ($C_1$-$C_6$)-alkyl, ($C_2$-$C_6$)-alkenyl or ($C_2$-$C_6$)-alkynyl, each of which is substituted by s radicals from the group consisting of nitro, halogen, cyano, thiocyanato, ($C_3$-$C_6$)-cycloalkyl, $R^1(O)C$, $R^1(R^1ON=)C$, $R^1O(O)C$, $(R^1)_2N(O)C$, $R^1(R^1O)N(O)C$, $R^2(O)_2S(R^1)N(O)C$, $R^1O(O)_2S(R^1)N(O)C$, $(R^1)_2N(O)_2S(R^1)N(O)C$, $R^1S(O)C$, $R^1O$, $R^1(O)CO$, $R^2(O)_2SO$, $R^2O(O)CO$, $(R^1)_2N(O)CO$, $(R^1)_2N$, $R^1O(R^1)N$, $R^1(O)C(R^1)N$, $R^2(O)_2S(R^1)N$, $R^2O(O)C(R^1)N$, $(R^1)_2N(O)C(R^1)N$, $R^1O(O)_2S(R^1)N$, $(R^1)_2N(O)_2S(R^1)N$, $R^2(O)_nS$, $R^1C(O)S$, $R^1O(O)_2S$, $(R^1)_2N(O)_2S$, $R^1(O)C(R^1)N(O)_2S$, $R^2O(O)C(R^1)N(O)_2S$, $(R^1)_2N(O)C(R^1)N(O)_2S$ and $(R^5O)_2(O)P$, or ($C_3$-$C_6$)-cycloalkyl, ($C_3$-$C_6$)-cycloalkenyl, phenyl, phenyl-($C_1$-$C_6$)-alkyl, heteroaryl, heteroaryl-($C_1$-$C_6$)-alkyl, heterocyclyl, heterocyclyl-($C_1$-$C_6$)-alkyl, phenyl-O—($C_1$-$C_6$)-alkyl, heteroaryl-O—($C_1$-$C_6$)-alkyl, heterocyclyl-O—($C_1$-$C_6$)-alkyl, phenyl-$N(R^1)$—($C_1$-$C_6$)-alkyl, heteroaryl-$N(R^1)$—($C_1$-$C_6$)-alkyl, heterocyclyl-$N(R^1)$—($C_1$-$C_6$)-alkyl, phenyl-$S(O)_n$—($C_1$-$C_6$)-alkyl, heteroaryl-$S(O)_n$—($C_1$-$C_6$)-alkyl or heterocyclyl-$S(O)_n$—($C_1$-$C_6$)-alkyl, each of which is substituted in the cyclic moiety by s radicals from the group consisting of nitro, halogen, cyano, thiocyanato, ($C_1$-$C_6$)-alkyl, halo-($C_1$-$C_6$)-alkyl, ($C_3$-$C_6$)-cycloalkyl, $R^1(O)C$, $R^1(R^1ON=)C$, $R^1O(O)C$, $(R^1)_2N(O)C$, $R^1(R^1O)N(O)C$, $R^2(O)_2S(R^1)N(O)C$, $R^1O(O)_2S(R^1)N(O)C$, $(R^1)_2N(O)_2S(R^1)N(O)C$, $R^1S(O)C$, $R^1O$, $R^1(O)CO$, $R^2(O)_2SO$, $R^2O(O)CO$, $(R^1)_2N(O)CO$, $(R^1)_2N$, $R^1O(R^1)N$, $R^1(O)C(R^1)N$, $R^2(O)_2S(R^1)N$, $R^2O(O)C(R^1)N$, $(R^1)_2N(O)C(R^1)N$, $R^1O(O)_2S(R^1)N$, $(R^1)_2N(O)_2S(R^1)N$, $R^2(O)_nS$, $R^1C(O)S$, $R^1O(O)_2S$, $(R^1)_2N(O)_2S$, $R^1(O)C(R^1)N(O)_2S$, $R^2O(O)C(R^1)N(O)_2S$, $(R^1)_2N(O)C(R^1)N(O)_2S$, $(R^5O)_2(O)P$ and $R^1O$—($C_1$-$C_6$)-alkyl, and where heterocyclyl carries n oxo groups, $R^9$ represents hydrogen, nitro, halogen, cyano, ($C_1$-$C_6$)-alkyl, halo-($C_1$-$C_6$)-alkyl, ($C_3$-$C_6$)-alkenyl, halo-($C_3$-$C_6$)-alkenyl, ($C_2$-$C_6$)-alkynyl, halo-($C_3$-$C_6$)-alkynyl, ($C_3$-$C_6$)-cycloalkyl, halo-($C_3$-$C_6$)-cycloalkyl, ($C_3$-$C_6$)-cycloalkyl-($C_1$-$C_6$)-alkyl, halo-($C_3$-$C_6$)-cycloalkyl-($C_1$-$C_6$)-alkyl, $R^1(O)C$, $R^2O(O)C$, $(R^1)_2N(O)C$, $R^2S(O)C$, $(R^1)_2N(S)C$, $R^1(R^1O)N(O)C$, $R^2(O)_2S(R^1)N(O)C$, $(R^1)_2N(O)_2S(R^1)N(O)C$, $R^1O$, $(R^1)_2N$, $R^2(O)_nS$, $(R^2)_3Si$—($C_1$-$C_6$)-alkyl-$(O)_nS$, $R^1O(O)_2S$, $(R^1)_2N(O)_2S$, $R^1(O)C(R^1)N(O)_2S$, $R^2O(O)C(R^1)N(O)_2S$, $(R^1)_2N(O)C(R^1)N(O)_2S$, $R^2(O)_2S(R^1)N(O)_2S$, $(R^5O)_2(O)P$, $(R^2)_3Si$, $R^1(O)C$—($C_1$-$C_6$)-alkyl, $R^1O(O)C$—($C_1$-$C_6$)-alkyl, $(R^1)_2N(O)C$—($C_1$-$C_6$)-alkyl, $(R^1O)(R^1)N(O)C$—($C_1$-$C_6$)- alkyl, $R^2(O)_2S(R^1)N(O)C\text{—}(C_1\text{-}C_6)$-alkyl, $R^1O(O)_2S(R_1)N(O)C\text{—}(C_1\text{-}C_6)$-alkyl, $(R^1)_2N(O)_2S(R^1)N(O)C\text{—}(C_1\text{-}C_6)$-alkyl, $R^1O\text{—}(C_1\text{-}C_6)$-alkyl, $R^1(O)CO\text{—}(C_1\text{-}C_6)$-alkyl, $R^2(O)_2SO\text{—}(C_1\text{-}C_6)$-alkyl, $R^2O(O)CO\text{—}(C_1\text{-}C_6)$-alkyl, $(R^1)_2N(O)CO\text{—}(C_1\text{-}C_6)$-alkyl, $(R^1)_2N\text{—}(C_1\text{-}C_6)$-alkyl, $R^1(O)C(R^1)N\text{—}(C_1\text{-}C_6)$-alkyl, $R^2(O)_2S(R^1)N\text{—}(C_1\text{-}C_6)$-alkyl, $R^2O(O)C(R^1)N\text{—}(C_1\text{-}C_6)$-alkyl, $(R^1)_2N(O)C(R^1)N\text{—}(C_1\text{-}C_6)$-alkyl, $R^1O(O)_2S(R^1)N\text{—}(C_1\text{-}C_6)$-alkyl, $(R^1)_2N(O)_2S(R^1)N\text{—}(C_1\text{-}C_6)$-alkyl, $R^2(O)_nS\text{—}(C_1\text{-}C_6)$-alkyl, $R^1O(O)_2S\text{—}(C_1\text{-}C_6)$-alkyl, $(R^1)_2N(O)_2S\text{—}(C_1\text{-}C_6)$-alkyl, $R^1(O)C(R^1)N(O)_2S\text{—}(C_1\text{-}C_6)$-alkyl, $R^2O(O)C(R^1)N(O)_2S\text{—}(C_1\text{-}C_6)$-alkyl, $(R^1)_2N(O)C(R^1)N(O)_2S\text{—}(C_1\text{-}C_6)$-alkyl, $(R^5O)_2(O)P\text{—}(C_1\text{-}C_6)$-alkyl, $(R^2)_3Si\text{—}(C_1\text{-}C_6)$-alkyl, or phenyl, heteroaryl, heterocyclyl, phenyl-$(C_1\text{-}C_6)$-alkyl, heteroaryl-$(C_1\text{-}C_6)$-alkyl or heterocyclyl-$(C_1\text{-}C_6)$-alkyl, each of which is substituted in the cyclic moiety by s radicals from the group consisting of nitro, halogen, cyano, thiocyanato, $(C_1\text{-}C_6)$-alkyl, halo-$(C_1\text{-}C_6)$-alkyl, $(C_3\text{-}C_6)$-cycloalkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O\text{—}(C_1\text{-}C_6)$-alkyl, and where heterocyclyl carries n oxo groups, m represents 0, 1, 2, 3 or 4, n represents 0, 1 or 2, s represents 0, 1, 2 or 3, except for compounds in which R and Y each represent hydrogen and at the same time
a) Z represents fluorine and X represents nitro, bromine or chlorine, or
b) Z represents chlorine and X represents chlorine, or
c) Z represents methoxy and X represents methoxy, or
d) Z represents ethoxy and X represents ethoxy, or
e) Z represents methyl sulfide and X represents methoxy.

DETAILED DESCRIPTION OF A PREFERRED EMBODIMENT

In the formula (I) and all the formulae which follow, alkyl radicals having more than two carbon atoms may be straight-chain or branched. Alkyl radicals are, for example, methyl, ethyl, n- or i-propyl, n-, i-, t- or 2-butyl, pentyls, hexyls such as n-hexyl, i-hexyl and 1,3-dimethylbutyl. Halogen is fluorine, chlorine, bromine or iodine.

Heterocyclyl is a saturated, partly saturated or fully unsaturated cyclic radical which contains 3 to 6 ring atoms, of which 1 to 4 are from the group of oxygen, nitrogen and sulfur, and which may additionally be fused by a benzo ring. For example, heterocyclyl is piperidinyl, pyrrolidinyl, tetrahydrofuranyl, dihydrofuranyl and oxetanyl.

Heteroaryl represents an aromatic cyclic radical which contains 3 to 6 ring atoms, of which 1 to 4 are from the group of oxygen, nitrogen and sulfur, and which may additionally be fused by a benzo ring. For example, heteroaryl is benzimidazol-2-yl, furanyl, imidazolyl, isoxazolyl, isothiazolyl, oxazolyl, pyrazinyl, pyrimidinyl, pyridazinyl, pyridinyl, benzisoxazolyl, thiazolyl, pyrrolyl, pyrazolyl, thiophenyl, 1,2,3-oxadiazolyl, 1,2,4-oxadiazolyl, 1,2,5-oxadiazolyl, 1,3,4-oxadiazolyl, 1,2,4-triazolyl, 1,2,3-triazolyl, 1,2,5-triazolyl, 1,3,4-triazolyl, 1,2,4-triazolyl, 1,2,4-thiadiazolyl, 1,3,4-thiadiazolyl, 1,2,3-thiadiazolyl, 1,2,5-thiadiazolyl, 2H-1,2,3,4-tetrazolyl, 1H-1,2,3,4-tetrazolyl, 1,2,3,4-oxatriazolyl, 1,2,3,5-oxatriazolyl, 1,2,3,4-thiatriazolyl and 1,2,3,5-thiatriazolyl.

If a group is polysubstituted by radicals, this is understood to mean that this group is substituted by one or more identical or different radicals from those mentioned.

Depending on the nature of the substituents and the manner in which they are attached, the compounds of the general formula (I) may be present as stereoisomers. If, for example, one or more asymmetric carbon atoms are present, enantiomers and diastereomers may occur. Stereoisomers likewise occur when n is 1 (sulfoxides). Stereoisomers can be obtained from the mixtures obtained in the preparation by customary separation methods, for example by chromatographic separation processes. It is likewise possible to selectively prepare stereoisomers by using stereoselective reactions with use of optically active starting materials and/or auxiliaries. The invention also relates to all the stereoisomers and mixtures thereof that are encompassed by the general formula (I) but are not defined specifically.

Preference is given to compounds of the general formula (I) in which

A represents N or CY,

X represents nitro, halogen, cyano, thiocyanato, $(C_1\text{-}C_6)$-alkyl, halo-$(C_1\text{-}C_6)$-alkyl, $(C_2\text{-}C_6)$-alkenyl, halo-$(C_2\text{-}C_6)$-alkenyl, $(C_2\text{-}C_6)$-alkynyl, halo-$(C_3\text{-}C_6)$-alkynyl, $(C_3\text{-}C_6)$-cycloalkyl, halo-$(C_3\text{-}C_6)$-cycloalkyl, $C_1\text{-}C_6)$-alkyl-O—$(C_1\text{-}C_6)$-alkyl, $(C_3\text{-}C_6)$-cycloalkyl-$(C_1\text{-}C_6)$-alkyl, halo-$(C_3\text{-}C_6)$-cycloalkyl-$(C_1\text{-}C_6)$-alkyl, $COR^1$, $OR^2$, $OCOR^1$, $OSO_2R^2$, $S(O)_nR^2$, $SO_2OR^1$, $SO_2N(R^1)_2$, $NR^1SO_2R^2$, $NR^1COR^1$, $(C_1\text{-}C_6)$-alkyl-$S(O)_nR^2$, $(C_1\text{-}C_6)$-alkyl-$OR^1$, $(C_1\text{-}C_6)$-alkyl-$OCOR^1$, $(C_1\text{-}C_6)$-alkyl-$OSO_2R^2$, $(C_1\text{-}C_6)$-alkyl-$CO_2R^1$, $(C_1\text{-}C_6)$-alkyl-$SO_2OR^1$, $(C_1\text{-}C_6)$-alkyl-$CON(R^1)_2$, $(C_1\text{-}C_6)$-alkyl-$SO_2N(R^1)_2$, $(C_1\text{-}C_6)$-alkyl-$NR^1COR^1$ or $(C_1\text{-}C_6)$-alkyl-$NR^1SO_2R^2$, $(C_1\text{-}C_6)$-alkylheteroaryl, $(C_1\text{-}C_6)$-alkyl-heterocyclyl, where the two last-mentioned radicals each by s radicals from the group consisting of halogen, $(C_1\text{-}C_6)$-alkyl, halo-$(C_1\text{-}C_6)$-alkyl, $S(O)_n\text{—}(C_1\text{-}C_6)$-alkyl, $(C_1\text{-}C_6)$-alkoxy and halo-$(C_1\text{-}C_6)$-alkoxy, and where heterocyclyl carries 0 to 2 oxo groups, Y represents hydrogen, nitro, halogen, cyano, thiocyanato, $(C_1\text{-}C_6)$-alkyl, halo-$(C_1\text{-}C_6)$-alkyl, $(C_2\text{-}C_6)$-alkenyl, halo-$(C_2\text{-}C_6)$-alkenyl, $(C_2\text{-}C_6)$-alkynyl, halo-$(C_3\text{-}C_6)$-alkynyl, $(C_3\text{-}C_6)$-cycloalkyl, $(C_3\text{-}C_6)$-cycloalkenyl, halo-$(C_3\text{-}C_6)$-cycloalkyl, $(C_3\text{-}C_6)$-cycloalkyl-$(C_1\text{-}C_6)$-alkyl, halo-$(C_3\text{-}C_6)$-cycloalkyl-$(C_1\text{-}C_6)$-alkyl, $COR^1$, $OR^1$, $COOR^1$, $OSO_2R^2$, $S(O)_nR^2$, $SO_2OR^1$, $SO_2N(R^1)_2$, $N(R^1)_2$, $NR^1SO_2R^2$, $NR^1COR^1$, $(C_1\text{-}C_6)$-alkyl-$S(O)_nR^2$, $(C_1\text{-}C_6)$-alkyl-$OR^1$, $(C_1\text{-}C_6)$-alkyl-$OCOR^1$, $(C_1\text{-}C_6)$-alkyl-$OSO_2R^2$, $(C_1\text{-}C_6)$-alkyl-$CO_2R^1$, $(C_1\text{-}C_6)$-alkyl-$SO_2OR^1$, $(C_1\text{-}C_6)$-alkyl-$CON(R^1)_2$, $(C_1\text{-}C_6)$-alkyl-$SO_2N(R^1)_2$, $(C_1\text{-}C_6)$-alkyl-$NR^1COR^1$, $(C_1\text{-}C_6)$-alkyl-$NR^1SO_2R^2$, $(C_1\text{-}C_6)$-alkylphenyl, $(C_1\text{-}C_6)$-alkyl-heteroaryl, $(C_1\text{-}C_6)$-alkyl-heterocyclyl, phenyl, heteroaryl or heterocyclyl, where the 6 last-mentioned radicals are each substituted by s radicals from the group consisting of halogen, nitro, cyano, $(C_1\text{-}C_6)$-alkyl, halo-$(C_1\text{-}C_6)$-alkyl, $(C_3\text{-}C_6)$-cycloalkyl, $S(O)_n\text{—}(C_1\text{-}C_6)$-alkyl, $(C_1\text{-}C_6)$-alkoxy, halo-$(C_1\text{-}C_6)$-alkoxy, $(C_1\text{-}C_6)$-alkoxy-$(C_1\text{-}C_4)$-alkyl and cyanomethyl, and where heterocyclyl carries 0 to 2 oxo groups, Z represents halogen, cyano, thiocyanato, nitro, $(C_1\text{-}C_6)$-alkyl, $(C_1\text{-}C_6)$-alkoxy, halo-$(C_1\text{-}C_6)$-alkyl, $(C_2\text{-}C_6)$-alkenyl, halo-$(C_2\text{-}C_6)$-alkenyl, $(C_2\text{-}C_6)$-alkynyl, halo-$(C_3\text{-}C_6)$-alkynyl, $(C_3\text{-}C_6)$-cycloalkyl, halo-$(C_3\text{-}C_6)$-cycloalkyl, $(C_3\text{-}C_6)$-cycloalkyl-$(C_1\text{-}C_6)$-alkyl, halo-$(C_3\text{-}C_6)$-cycloalkyl-$(C_1\text{-}C_6)$-alkyl, $COR^1$, $COOR^1$, $C(O)N(R^1)_2$, $C(O)NR^1OR^1$, $OSO_2R^2$, $S(O)_nR^2$, $SO_2OR^1$, $SO_2N(R^1)_2$, $NR^1SO_2R^2$, $NR^1COR^1$, $(C_1\text{-}C_6)$-alkyl-$S(O)_nR^2$, $(C_1\text{-}C_6)$-alkyl-$OR^1$, $(C_1\text{-}C_6)$-alkyl-$OCOR^1$, $(C_1\text{-}C_6)$-alkyl-$OSO_2R^2$, $(C_1\text{-}C_6)$-alkyl-$CO_2R^1$, $(C_1\text{-}C_6)$-alkyl-$SO_2OR^1$, $(C_1\text{-}C_6)$-alkyl-$CON(R^1)_2$, $(C_1\text{-}C_6)$-alkyl-$SO_2N(R^1)_2$, $(C_1\text{-}C_6)$-alkyl-$NR^1COR^1$, $(C_1\text{-}C_6)$-alkyl-$NR^1SO_2R^2$, 1,2,4-triazol-1-yl, or Z may also represent hydrogen if Y represents the $S(O)_nR^2$ radical, V represents hydrogen, $(C_1-C_6)$-alkyl, halo-$(C_1-C_6)$-alkyl, $(C_1-C_6)$-alkoxy, $(C_1-C_6)$-haloalkoxy, $S(O)_n$—$(C_1-C_6)$-alkyl, $S(O)_n$—$(C_1-C_6)$-haloalkyl, $(C_1-C_6)$-alkoxy-$(C_1-C_4)$-alkyl, halogen, nitro or cyano, R represents hydrogen, $(C_1-C_6)$-alkyl, $(C_3-C_7)$-cycloalkyl, halo-$(C_1-C_6)$-alkyl, $(C_1-C_6)$-alkoxy, halo-$(C_1-C_6)$-alkoxy, cyano-$(C_1-C_6)$-alkyl, cyano, methylsulfenyl, methylsulfinyl, methylsulfonyl, acetylamino, methoxymethyl, or heteroaryl, heterocyclyl or phenyl, each of which is substituted by s radicals from the group consisting of methyl, ethyl, methoxy, trifluoromethyl and halogen, $R^1$ represents hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl or $(C_1-C_6)$-alkyl-$NR^3$-heterocyclyl, where the 16 last-mentioned radicals are substituted by s radicals from the group consisting of cyano, halogen, nitro, $OR^3$, $S(O)_nR^4$, $N(R^3)_2$, $NR^3OR^3$, $COR^3$, $OCOR^3$, $NR^3COR^3$, $NR^3SO_2R^4$, $CO_2R^3$, $CON(R^3)_2$ and $(C_1-C_4)$-alkoxy-$(C_2-C_6)$-alkoxycarbonyl, and where heterocyclyl carries 0 to 2 oxo groups, $R^2$ represents $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl or $(C_1-C_6)$-alkyl-$NR^3$-heterocyclyl, where these radicals are substituted by s radicals from the group consisting of cyano, halogen, nitro, $OR^3$, $S(O)_nR^4$, $N(R^3)_2$, $NR^3OR^3$, $NR^3SO_2R^4$, $COR^3$, $OCOR^3$, $NR^3COR^3$, $CO_2R^3$, $CON(R^3)_2$ and $(C_1-C_4)$-alkoxy-$(C_2-C_6)$-alkoxycarbonyl, and where heterocyclyl carries 0 to 2 oxo groups, $R^3$ represents hydrogen, $(C_1-C_6)$-alkyl, $(C_2-C_6)$-alkenyl, $(C_2-C_6)$-alkynyl, $(C_3-C_6)$-cycloalkyl or $(C_3-C_6)$-cycloalkyl-$(C_1-C_6)$-alkyl, $R^4$ represents $(C_1-C_6)$-alkyl, $(C_2-C_6)$-alkenyl or $(C_2-C_6)$-alkynyl, $R^6$ and $R^7$ independently of one another each represent $(C_1-C_6)$-alkyl, halo-$(C_1-C_6)$-alkyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $(C_1-C_6)$-alkoxy-$(C_1-C_6)$-alkyl, halo-$(C_1-C_6)$-alkoxy-$(C_1-C_6)$-alkyl, phenyl, heteroaryl or heterocyclyl, where the three last-mentioned radicals are each substituted by s radicals from the group consisting of nitro, halogen, $(C_1-C_6)$-alkyl, halo-$(C_1-C_6)$-alkyl, $R^1O(O)C$, $(R^1)_2N(O)C$, $R^1O$, $(R^1)_2N$, $R^2(O)_nS$ and $R^1O$—$(C_1-C_6)$-alkyl, and where heterocyclyl carries n oxo groups, or $R^6$ and $R^7$ together with the sulfur atom to which they are attached form a 3- to 8-membered unsaturated, partly saturated or saturated ring which contains, in addition to the carbon atoms and in addition to the sulfur atom of the sulfoximino group, in each case m ring members from the group consisting of $N(R^1)$, 0 and $S(O)_n$, and where this ring is in each case substituted by s radicals from the group consisting of halogen, $(C_1-C_6)$-alkyl, halo-$(C_1-C_6)$-alkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O$—$(C_1-C_6)$-alkyl, and where this ring carries n oxo groups, $R^8$ represents $(C_1-C_6)$-alkyl which is in each case substituted by s radicals from the group consisting of halogen, cyano, $(C_3-C_6)$-cycloalkyl, $R^1(O)C$, $R^1(R^1ON=)C$, $R^1O(O)C$, $(R^1)_2N(O)C$, $R^2(O)_2S(R^1)N(O)C$, $R^1O$, $(R^1)_2N$, $R^1(O)C(R^1)N$, $R^2(O)_2S(R^1)N$, $R^2O(O)C(R^1)N$, $(R^1)_2N(O)C(R^1)N$, $R^2(O)_nS$, $R^1O(O)_2S$, $(R^1)_2N(O)_2S$, $R^1(O)C(R^1)N(O)_2S$, $R^2O(O)C(R^1)N(O)_2S$ and $(R^1)_2N(O)C(R^1)N(O)_2S$ or $(C_3-C_6)$-cycloalkyl which is in each case substituted by s radicals from the group consisting of halogen, $(C_1-C_6)$-alkyl, halo-$(C_1-C_6)$-alkyl, $(C_3-C_6)$-cycloalkyl, $R^1O(O)C$ and $(R^1)_2N(O)C$, $R^9$ represents hydrogen, nitro, cyano, $(C_1-C_6)$-alkyl, halo-$(C_1-C_6)$-alkyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $R^1(O)C$, $R^2O(O)C$, $(R^1)_2N(O)C$, $R^2(O)_2S$, $R^1(O)C$—$(C_1-C_6)$-alkyl, $R^1O(O)C$—$(C_1-C_6)$-alkyl, $(R^1)_2N(O)C$—$(C_1-C_6)$-alkyl, $R^1O$—$(C_1-C_6)$-alkyl, $(R^1)_2N$—$(C_1-C_6)$-alkyl or $R^2(O)_nS$—$(C_1-C_6)$-alkyl, m represents 0, 1 or 2, n represents 0, 1 or 2, s represents 0, 1, 2 or 3, except for compounds in which R and Y each represent hydrogen and at the same time a) Z represents fluorine and X represents nitro, bromine or chlorine, or b) Z represents chlorine and X represents chlorine, or c) Z represents methoxy and X represents methoxy, or d) Z represents ethoxy and X represents ethoxy, or e) Z represents methyl sulfide and X represents methoxy.

Particular preference is given to compounds of the general formula (I) in which

A represents N or CY,

X represents nitro, halogen, cyano, $(C_1-C_6)$-alkyl, halo-$(C_1-C_6)$-alkyl, $(C_3-C_6)$-cycloalkyl, $OR^2$, $S(O)_nR^2$, $(C_1-C_6)$-alkyl-$S(O)_nR^2$, $(C_1-C_6)$-alkyl-$OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $(C_1-C_6)$-alkylheteroaryl, $(C_1-C_6)$-alkylheterocyclyl, where the two last-mentioned radicals are each substituted by s radicals from the group consisting of halogen, $(C_1-C_6)$-alkyl, halo-$(C_1-C_6)$-alkyl, $S(O)_n$—$(C_1-C_6)$-alkyl, $(C_1-C_6)$-alkoxy, halo-$(C_1-C_6)$-alkoxy, and where heterocyclyl carries 0 to 2 oxo groups, Y hydrogen, nitro, halogen, cyano, $(C_1-C_6)$-alkyl, $(C_1-C_6)$-haloalkyl, $OR^1$, $S(O)_nR^2$, $SO_2N(R^1)_2$, $N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $(C_1-C_6)$-alkylphenyl, $(C_1-C_6)$-alkylheteroaryl, $(C_1-C_6)$-alkylheterocyclyl, phenyl, heteroaryl or heterocyclyl, where the 6 last-mentioned radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl carries 0 to 2 oxo groups, Z represents halogen, cyano, nitro, $(C_1-C_6)$-alkyl, $(C_1-C_6)$-alkoxy, halo-$(C_1-C_6)$-alkyl, $(C_3-C_6)$-cycloalkyl, $S(O)_nR^2$, 1,2,4-triazol-1-yl, or Z may also represent hydrogen if Y represents the $S(O)_nR^2$ radical, V represents hydrogen, $(C_1-C_6)$-alkyl, halo-$(C_1-C_6)$-alkyl, $(C_1-C_6)$-alkoxy, $(C_1-C_6)$-haloalkoxy, $S(O)_n$—$(C_1-C_6)$-alkyl, $S(O)_n$—$(C_1-C_6)$-haloalkyl, $(C_1-C_6)$-alkoxy-$(C_1-C_4)$-alkyl, halogen, nitro or cyano, R represents hydrogen, $(C_1-C_6)$-alkyl, $(C_3-C_7)$-cycloalkyl, halo-$(C_1-C_6)$-alkyl, $(C_1-C_6)$-alkoxy, halo-$(C_1-C_6)$-alkoxy, cyano-$(C_1-C_6)$-alkyl, cyano, methylsulfenyl, methylsulfinyl, methylsulfonyl, acetylamino, halogen, amino, methoxymethyl, $R^1$ represents hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl or $(C_1-C_6)$-alkyl-$NR^3$-heterocyclyl, where the 16 last-mentioned radicals are substituted by s radicals from the group consisting of cyano, halogen, nitro, $OR^3$, $S(O)_nR^4$, $N(R^3)_2$, $NR^3OR^3$, $COR^3$, $OCOR^3$, $NR^3COR^3$, $NR^3SO_2R^4$, $CO_2R^3$, $CON(R^3)_2$ and $(C_1-C_4)$-alkoxy-$(C_2-C_6)$-alkoxycarbonyl, and where heterocyclyl carries 0 to 2 oxo groups, $R^2$ represents $(C_1-C_6)$-alkyl, $(C_3-C_6)$-cycloalkyl or $(C_3-C_6)$-cycloalkyl-$(C_1-C_6)$-alkyl, where these three radicals mentioned above are each substituted by s radicals from the group consisting of halogen and $OR^3$, $R^3$ represents hydrogen or $(C_1-C_6)$-alkyl, $R^4$ represents $(C_1-C_6)$-alkyl, $R^6$ and $R^7$ independently of one another each represent methyl, ethyl or n-propyl, or $R^6$ and $R^7$ together with the sulfur atom to which they are attached form a 5- or 6-membered saturated ring which, in addition to the carbon atoms and in addition to the sulfur atom of the sulfoximino group, contains m oxygen atoms, $R^8$ represents methyl, ethyl or n-propyl, $R^9$ represents hydrogen or cyano, m represents 0 or 1, n represents 0, 1 or 2, s represents 0, 1, 2 or 3, except for compounds in which R and Y each represent hydrogen and at the same time a) Z represents fluorine and X represents nitro, bromine or chlorine, or b) Z represents chlorine and X represents chlorine, or c) Z represents methoxy and X represents methoxy, or d) Z represents ethoxy and X represents ethoxy, or e) Z represents methyl sulfide and X represents methoxy.

In all the formulae specified hereinafter, the substituents and symbols have the same meaning as described in formula (I), unless defined differently.

Compounds according to the invention can be prepared, for example, by the method shown in scheme 1, by base-catalyzed reaction of a benzoyl chloride (II) with a 3-aminoisoxazole (III):

Scheme 1

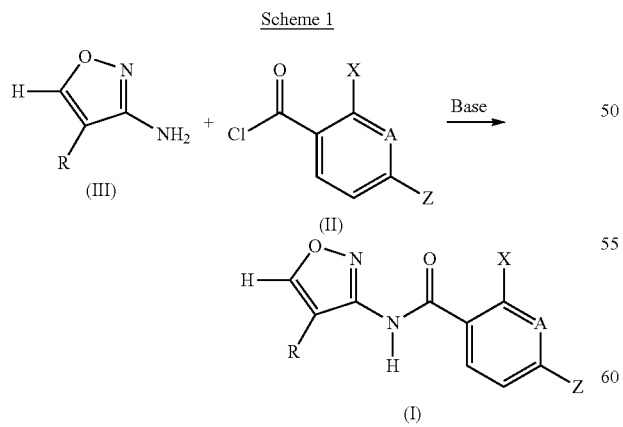

Compounds according to the invention can also be prepared by the method described in scheme 2, by reacting a benzoic acid of the formula (IV) with a 3-aminoisoxazole (III):

Scheme 2

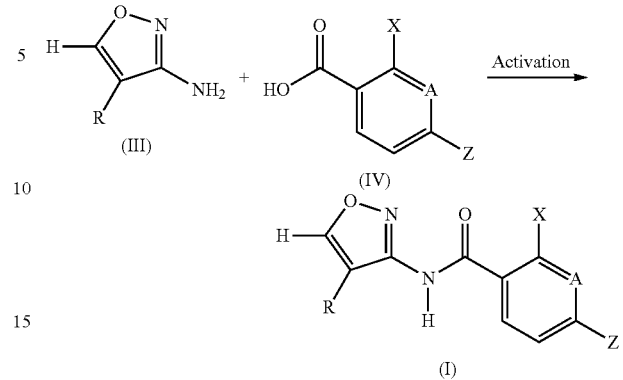

For the activation, it is possible to use dehydrating reagents which are typically for amidation reactions, for example 1,1'-carbonyldiimidazole (CDI), dicyclohexylcarbodiimide (DCC), 2,4,6-tripropyl-1,3,5,2,4,6-trioxatriphosphinane 2,4,6-trioxide (T3P), etc.

It may be expedient to change the order of reaction steps. Thus, benzoic acids carrying a sulfoxide cannot be converted directly into their acid chlorides. Here, it is advisable to prepare initially, at the thioether stage, the amide and then to oxidize the thioether to the sulfoxide.

The benzoyl chlorides of the formula (II) or the parent benzoic acids thereof (IV) are known in principle and can be prepared, for example, by the methods described in U.S. Pat. No. 6,376,429 B1, EP 1 585 742 A1 and EP 1 202 978 A1.

The 3-aminoisoxazoles of the formula (III) are either commercially available or can be prepared analogously to methods known from the literature.

For example, 3-amino-4-R-isoxazoles can be prepared by the method described in Monatshefte für Chemie 1970, 101 (4), p. 1109, from a substituted acrylonitrile (V):

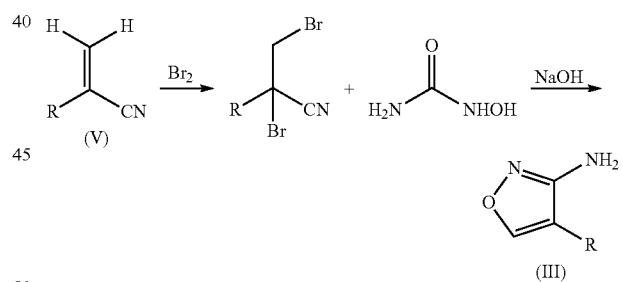

In the abovementioned formula, R is, for example, an alkyl radical.

3-Aminoisoxazoles of the formula (III) in which R represents halogen can be prepared, for example, as described in WO2010/68453 by halogenation of 3-aminoisoxazole (VI) using customary halogenating agents such as, for example, $Cl_2$, $Br_2$ or N-halosuccinimides:

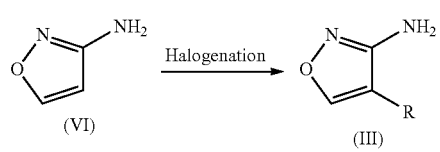

Collections of compounds of the formula (I) and/or salts thereof which can be synthesized by the abovementioned reactions can also be prepared in a parallelized manner, in which case this may be accomplished in a manual, partly automated or fully automated manner. It is possible, for example, to automate the conduct of the reaction, the work-up or the purification of the products and/or intermediates. Overall, this is understood to mean a procedure as described, for example, by D. Tiebes in Combinatorial Chemistry—Synthesis, Analysis, Screening (editor Günther Jung), Wiley, 1999, on pages 1 to 34.

For the parallelized conduct of the reaction and workup, it is possible to use a number of commercially available instruments, for example Calypso reaction blocks from Barnstead International, Dubuque, Iowa 52004-0797, USA or reaction stations from Radleys, Shirehill, Saffron Walden, Essex, CB11 3AZ, England, or MultiPROBE Automated Workstations from PerkinElmer, Waltham, Mass. 02451, USA. For the parallelized purification of compounds of the general formula (I) and salts thereof or of intermediates which occur in the course of preparation, available apparatuses include chromatography apparatuses, for example from ISCO, Inc., 4700 Superior Street, Lincoln, Nebr. 68504, USA.

The apparatuses detailed lead to a modular procedure in which the individual working steps are automated, but manual operations have to be carried out between the working steps. This can be circumvented by using partly or fully integrated automation systems in which the respective automation modules are operated, for example, by robots. Automation systems of this type can be obtained, for example, from Caliper, Hopkinton, Mass. 01748, USA.

The implementation of single or multiple synthesis steps can be supported by the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Aside from the methods described here, compounds of the general formula (I) and salts thereof can be prepared completely or partially by solid-phase-supported methods. For this purpose, individual intermediates or all intermediates in the synthesis or a synthesis adapted for the corresponding procedure are bound to a synthesis resin. Solid-phase-supported synthesis methods are described adequately in the technical literature, for example Barry A. Bunin in "The Combinatorial Index", Academic Press, 1998 and Combinatorial Chemistry—Synthesis, Analysis, Screening (editor: Günther Jung), Wiley, 1999. The use of solid-phase-supported synthesis methods permits a number of protocols, which are known from the literature and which for their part may be performed manually or in an automated manner. The reactions can be performed, for example, by means of IRORI technology in microreactors from Nexus Biosystems, 12140 Community Road, Poway, Calif. 92064, USA.

Both in the solid and in the liquid phase, individual or several synthesis steps may be supported by the use of microwave technology. The specialist literature describes a series of experimental protocols, for example in Microwaves in Organic and Medicinal Chemistry (editor: C. O. Kappe and A. Stadler), Wiley, 2005.

The preparation by the processes described here gives compounds of the formula (I) and salts thereof in the form of substance collections, which are called libraries. The present invention also provides libraries comprising at least two compounds of the formula (I) and salts thereof.

The compounds of the formula (I) according to the invention (and/or salts thereof), referred to collectively as "compounds according to the invention" hereinafter, have excellent herbicidal efficacy against a broad spectrum of economically important monocotyledonous and dicotyledonous annual harmful plants. The active compounds also have good control over perennial harmful plants which are difficult to control and produce shoots from rhizomes, root stocks or other perennial organs.

The present invention therefore also provides a method for controlling unwanted plants or for regulating the growth of plants, preferably in plant crops, in which one or more compound(s) according to the invention is/are applied to the plants (for example harmful plants such as monocotyledonous or dicotyledonous weeds or unwanted crop plants), the seed (for example grains, seeds or vegetative propagules such as tubers or shoot parts with buds) or the area on which the plants grow (for example the area under cultivation). The compounds according to the invention can be deployed, for example, prior to sowing (if appropriate also by incorporation into the soil), prior to emergence or after emergence. Specific examples of some representatives of the monocotyledonous and dicotyledonous weed flora which can be controlled by the compounds according to the invention are as follows, though the enumeration is not intended to impose a restriction to particular species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the compounds according to the invention are applied to the soil surface before germination, either the emergence of the weed seedlings is prevented completely or the weeds grow until they have reached the cotyledon stage, but then they stop growing and ultimately die completely after three to four weeks have passed.

If the active compounds are applied post-emergence to the green parts of the plants, growth stops after the treatment, and the harmful plants remain at the growth stage of the time of application, or they die completely after a certain time, such that competition by the weeds, which is harmful to the crop plants, is thus eliminated very early and in a lasting manner.

Although the compounds according to the invention have outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum,*

*Solanum, Vicia,* or monocotyledonous crops of the genera *Allium, Ananas, Asparagus, Avena, Hordeum, Oryza, Panicum, Saccharum, Secale, Sorghum, Triticale, Triticum, Zea,* in particular *Zea* and *Triticum*, will be damaged to a negligible extent only, if at all, depending on the structure of the particular compound according to the invention and its application rate. For these reasons, the present compounds are very suitable for selective control of unwanted plant growth in plant crops such as agriculturally useful plants or ornamental plants.

In addition, the compounds according to the invention (depending on their particular structure and the application rate deployed) have outstanding growth-regulating properties in crop plants. They intervene in the plants' own metabolism with regulatory effect, and can thus be used for controlled influencing of plant constituents and to facilitate harvesting, for example by triggering desiccation and stunted growth. In addition, they are also suitable for general control and inhibition of unwanted vegetative growth without killing the plants. Inhibition of vegetative growth plays a major role for many mono- and dicotyledonous plants since, for example, this can reduce or completely prevent lodging.

By virtue of their herbicidal and plant growth regulatory properties, the active compounds can also be used to control harmful plants in crops of genetically modified plants or plants modified by conventional mutagenesis. In general, transgenic plants are notable for particular advantageous properties, for example for resistances to certain pesticides, in particular certain herbicides, resistances to plant diseases or pathogens of plant diseases, such as certain insects or microorganisms such as fungi, bacteria or viruses. Other particular properties relate, for example, to the harvested material with regard to quantity, quality, storability, composition and specific constituents. For instance, there are known transgenic plants with an elevated starch content or altered starch quality, or with a different fatty acid composition in the harvested material.

It is preferable, with respect to transgenic crops, to use the compounds according to the invention in economically important transgenic crops of useful plants and ornamentals, for example of cereals such as wheat, barley, rye, oats, millet/sorghum, rice and corn or else crops of sugar beet, cotton, soybean, oilseed rape, potato, tomato, peas and other types of vegetable. It is preferred to employ the compounds according to the invention as herbicides in crops of useful plants which are resistant, or have been made resistant by recombinant means, to the phytotoxic effects of the herbicides.

Preference is given to the use of the compounds according to the invention or salts thereof in economically important transgenic crops of useful plants and ornamentals, for example of cereals such as wheat, barley, rye, oats, millet/sorghum, rice, cassava and corn, or else crops of sugar beet, cotton, soybean, oilseed rape, potato, tomato, peas and other types of vegetable. Preferably, the compounds according to the invention can be used as herbicides in crops of useful plants which are resistant, or have been made resistant by genetic engineering, to the phytotoxic effects of the herbicides.

Conventional ways of producing novel plants which have modified properties in comparison to plants which have occurred to date consist, for example, in traditional breeding methods and the generation of mutants. Alternatively, novel plants with altered properties can be generated with the aid of recombinant methods (see, for example, EP-A-0221044, EP-A-0131624). For example, there have been descriptions in several cases of:

genetic modifications of crop plants for the purpose of modifying the starch synthesized in the plants (e.g. WO 92/11376, WO 92/14827, WO 91/19806), transgenic crop plants which are resistant to particular herbicides of the glufosinate type (cf., for example, EP-A-0242236, EP-A-242246) or glyphosate type (WO 92/00377) or of the sulfonylureas (EP-A-0257993, USA 5013659), transgenic crop plants, for example cotton, capable of producing *Bacillus thuringiensis* toxins (Bt toxins), which make the plants resistant to particular pests (EP-A-0142924, EP-A-0193259), transgenic crop plants with a modified fatty acid composition (WO 91/13972), genetically modified crop plants with novel constituents or secondary metabolites, for example novel phytoalexins, which bring about an increased disease resistance (EPA 309862, EPA0464461), genetically modified plants having reduced photorespiration, which have higher yields and higher stress tolerance (EPA 0305398), transgenic crop plants which produce pharmaceutically or diagnostically important proteins ("molecular pharming"), transgenic crop plants which feature higher yields or better quality, transgenic crop plants which feature a combination, for example, of the abovementioned novel properties ("gene stacking").

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431.

For such recombinant manipulations, nucleic acid molecules which allow mutagenesis or sequence alteration by recombination of DNA sequences can be introduced into plasmids. With the aid of standard methods, it is possible, for example, to undertake base exchanges, remove parts of sequences or add natural or synthetic sequences. For the joining of the DNA fragments to one another, adaptors or linkers can be attached to the fragments; see, for example, Sambrook et al., 1989, Molecular Cloning, A Laboratory Manual, 2nd ed. Cold Spring Harbor Laboratory Press, Cold Spring Harbor, N.Y.; or Winnacker "Gene and Klone" [Genes and Clones], VCH Weinheim 2nd edition 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product. To this end, it is firstly possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. It is also possible to use DNA sequences which have a high degree of homology to the coding sequences of a gene product, but are not completely identical to them.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850, Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants may be plants of any desired plant species, i.e. not only monocotyledonous but also dicotyledonous plants.

Thus, transgenic plants can be obtained whose properties are altered by overexpression, suppression or inhibition of homologous (=natural) genes or gene sequences or expression of heterologous (=foreign) genes or gene sequences.

The compounds according to the invention can be used with preference in transgenic crops which are resistant to growth regulators, for example dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active compounds.

When the active compounds according to the invention are used in transgenic crops, not only do the effects toward harmful plants which are observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also provides for the use of the compounds according to the invention as herbicides for control of harmful plants in transgenic crop plants.

The compounds according to the invention can be applied in the form of wettable powders, emulsifiable concentrates, sprayable solutions, dusting products or granules in the customary formulations. The invention therefore also provides herbicidal and plant-growth-regulating compositions which comprise the compounds according to the invention.

The compounds according to the invention can be formulated in various ways, according to the biological and/or physicochemical parameters required. Possible formulations include, for example: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical Technology], volume 7, C. Hanser Verlag Munich, 4th ed. 1986; Wade van Valkenburg, "Pesticide Formulations", Marcel Dekker, N.Y., 1973; K. Martens, "Spray Drying" Handbook, 3rd ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd ed., Darland Books, Caldwell N.J.; H. v. Olphen, "Introduction to Clay Colloid Chemistry", 2nd ed., J. Wiley & Sons, N.Y.; C. Marsden, "Solvents Guide", 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active Ethylene Oxide Adducts], Wiss. Verlagsgesellschaft, Stuttgart 1976; Winnacker-Küchler, "Chemische Technologie" [Chemical Engineering], volume 7, C. Hanser Verlag Munich, 4th ed. 1986.

On the basis of these formulations, it is also possible to produce combinations with other pesticidally active substances, for example insecticides, acaricides, herbicides, fungicides, and also with safeners, fertilizers and/or growth regulators, for example in the form of a finished formulation or as a tankmix. Suitable safeners are, for example, mefenpyr-diethyl, cyprosulfamide, isoxadifen-ethyl, cloquintocetmexyl and dichlormid.

Wettable powders are preparations which can be dispersed uniformly in water and, in addition to the active compound, apart from a diluent or inert substance, also comprise surfactants of the ionic and/or nonionic type (wetting agents, dispersants), for example polyoxyethylated alkylphenols, polyoxyethlated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To produce the wettable powders, the herbicidally active compounds are finely ground, for example in customary apparatus such as hammer mills, blower mills and air-jet mills, and simultaneously or subsequently mixed with the formulation auxiliaries.

Emulsifiable concentrates are produced by dissolving the active compound in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). Examples of emulsifiers which may be used are: calcium alkylarylsulfonate salts such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dustable powders are obtained by grinding the active compound with finely distributed solid substances, for example talc, natural clays such as kaolin, bentonite and pyrophyllite, or diatomaceous earth.

Suspension concentrates may be water- or oil-based. They may be prepared, for example, by wet-grinding by means of commercial bead mills and optional addition of surfactants as have, for example, already been listed above for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be prepared either by spraying the active compound onto adsorptive granular inert material or by applying active compound concentrates to the surface of carriers, such as sand, kaolinites or granular inert material, by means of adhesives, for example polyvinyl alcohol, sodium polyacrylate or else mineral oils. Suitable active compounds can also be granulated in the manner customary for the production of fertilizer granules—if desired as a mixture with fertilizers.

Water-dispersible granules are produced generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London, J. E. Browning, "Agglomeration", Chemical and Engineering 1967, pages 147 ff.; "Perry's Chemical Engineer's Handbook", 5th ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th ed., Blackwell Scientific Publications, Oxford, 1968, pages 101-103.

The agrochemical preparations contain generally 0.1 to 99% by weight, especially 0.1 to 95% by weight, of compounds according to the invention.

In wettable powders, the active compound concentration is, for example, about 10 to 90% by weight, the remainder to 100% by weight consisting of customary formulation constituents. In emulsifiable concentrates, the active compound concentration may be about 1 to 90% and preferably 5 to 80% by weight. Dust-type formulations contain 1% to 30% by weight of active compound, preferably usually 5% to 20% by weight of active compound; sprayable solutions contain about 0.05% to 80% by weight, preferably 2% to 50% by weight of active compound. In the case of water-dispersible granules, the active compound content depends partially on whether the active compound is present in liquid or solid form and on which granulation auxiliaries, fillers, etc., are used. In the water-dispersible granules, the content of active compound is, for example, between 1 and 95% by weight, preferably between 10 and 80% by weight.

In addition, the active compound formulations mentioned optionally comprise the respective customary stickers, wetters, dispersants, emulsifiers, penetrants, preservatives, antifreeze agents and solvents, fillers, carriers and dyes, defoamers, evaporation inhibitors and agents which influence the pH and the viscosity.

On the basis of these formulations, it is also possible to produce combinations with other pesticidally active substances, for example insecticides, acaricides, herbicides, fungicides, and also with safeners, fertilizers and/or growth regulators, for example in the form of a finished formulation or as a tankmix.

For application, the formulations in commercial form are, if appropriate, diluted in a customary manner, for example in the case of wettable powders, emulsifiable concentrates, dispersions and water-dispersible granules with water. Dust-type formulations, granules for soil application or granules for scattering and sprayable solutions are not normally diluted further with other inert substances prior to application.

The required application rate of the compounds of the formula (I) varies with the external conditions, including temperature, humidity and the type of herbicide used. It can vary within wide limits, for example between 0.001 and 1.0 kg/ha or more of active substance, but it is preferably between 0.005 and 750 g/ha.

The examples which follow illustrate the invention.

A. CHEMICAL EXAMPLES

Synthesis of 2,4-difluoro-N-(1,2-oxazol-3-yl)benzamide (Table Example 1-1)

At 0-5° C., 346 mg (1.96 mmol) of 2,4-difluorobenzoyl chloride are added to a solution of 150 mg (1.78 mmol) of 1,2-oxazole-3-amine and 11 mg (0.089 mmol) of 4-dimethylaminopyridine in 5 ml of dichloromethane. The reaction mixture is stirred at 5° C. for 3 h and then overnight at room temperature. 5 ml of water are then added, and the mixture is extracted three times with 5 ml of dichloromethane each time. The combined organic phases are dried over magnesium sulfate, filtered and concentrated. The residue is purified by column chromatography (silica gel, heptane, ethyl acetate). Yield 233 mg (57%).

$^1$H-NMR, DMSO-$d_6$, 400 MHz: 11.49 (s, 1H), 8.87 (s, 1H), 7.79 (ddd, 1H), 7.42 (td, 1H), 7.22 (td, 1H), 7.01 (s, 1H).

Synthesis of 2-chloro-4-(methylsulfonyl)-N-(1,2-oxazol-3-yl)-3-[(2,2,2-trifluoroethoxy)methyl]benzamide, (Table Example No. 1-334)

825 mg (2.38 mmol) of 2-chloro-4-(methylsulfonyl)-3-[(2,2,2-trifluoroethoxy)methyl]benzoic acid and 200 mg (2.38 mmol) of 1,2-oxazole-3-amine are dissolved at room temperature (RT) in 20 ml of $CH_2Cl_2$, and 0.33 ml (2.38 mmol) of triethylamine, 58 mg (0.48 mmol) of DMAP and 2.271 g (3.57 mmol) of 2,4,6-tripropyl-1,3,5,2,4,6-trioxatriphosphinane 2,4,6-trioxide (50% solution in THF) are added. The reaction mixture is stirred at RT for 20 h and then washed twice with in each case 10 ml of water. The organic phase is dried over $Na_2SO_4$ and concentrated. The residue is purified by column chromatography (silica gel, heptane/ethyl acetate). Yield 240 mg (20%).

$^1$H-NMR, CDCl$_3$, 400 MHz: 9.50 (s, 1H), 8.32 (s, 1H), 8.22 (d, 1H), 7.79 (d, 1H), 5.38 (s, 2H), 4.05 (q, 2H), 3.23 (s, 3H), 2.45 (s, 3H)

Synthesis of 2-(methoxymethyl)-N-(1,2-oxazol-3-yl)-6-(trifluoromethyl)nicotinamide, (Table Example No. 10-3)

118 mg (0.5 mmol) of 2-methoxymethyl-4-trifluoromethylnicotinic acid and 42 mg (0.5 mmol) of 1,2-oxazole-3-amine are dissolved at RT in 10 ml of $CH_2Cl_2$, and 0.5 ml (2.5 mmol) of triethylamine, 12 mg (0.1 mmol) of DMAP and 1.5 ml (7.5 mmol) of 2,4,6-tripropyl-1,3,5,2,4,6-trioxatriphosphinane 2,4,6-trioxide (50% solution in THF) are added. The reaction mixture is stirred at RT for 20 h and then washed twice with in each case 5 ml of water. The organic phase is dried over $Na_2SO_4$ and concentrated. The residue is purified by column chromatography (silica gel, heptane/ethyl acetate). Yield 77 mg (51%).

$^1$H-NMR, DMSO-$d_6$, 400 MHz: 11.68 (s, 1H), 8.88 (s, 1H), 8.27 (d, 1H), 8.00 (d, 1H), 7.05 (s, 1H), 4.71 (s, 2H), 3.23 (s, 3H).

Synthesis of 2-chloro-N-[4-(2-cyanoethyl)-1,2-oxazol-3-yl]-3-[5-(cyanomethyl)-4,5-dihydro-1,2-oxazol-3-yl]-4-(ethylsulfonyl)benzamide, (Table Example No. 9-343)

300 mg (0.84 mmol) of 2-chloro-3-[5-(cyanomethyl)-4,5-dihydro-1,2-oxazol-3-yl]-4-(ethylsulfonyl)benzoic acid and 115 mg (0.84 mmol) of 3-(3-amino-1,2-oxazol-4-yl)propanonitrile are dissolved at RT in 20 ml of $CH_2Cl_2$, and 0.59 ml (4.20 mmol) of triethylamine, 21 mg (0.168 mmol) of DMAP and 0.803 g (1.26 mmol) of 2,4,6-tripropyl-1,3,5,2,4,6-trioxatriphosphinane 2,4,6-trioxide (50% solution in THF) are added. The reaction mixture is stirred at RT for 20 h and then washed twice with in each case 10 ml of water. The organic phase is dried over $Na_2SO_4$ and concentrated. The residue is purified by column chromatography (silica gel, heptane/ethyl acetate). Yield 230 mg (55%).

$^1$H-NMR, DMSO-$d_6$, 400 MHz: 11.23 (s, 1H), 8.88 (s, 1H), 8.11 (d, 1H), 8.09 (d, 1H), 5.8 (m, 1H), 3.61 (dd, 1H), 3.41 (q, 2H), 3.30 (s, 3H), 3.18 (dd, 1H), 3.01 (m, 2H), 2.81 (m, 4H), 1.15 (t, 3H).

Synthesis of 3-(3-amino-1,2-oxazol-4-yl)propanonitrile

At 0° C., 8.96 g (56.07 mmol) of bromine are slowly added dropwise to a solution of 7.0 g (65.96 mmol) of 2-methylenepentanedinitrile. The reaction mixture is then stirred at 35° C. for 2 hours. The reaction mixture is then once more cooled to 0° C., and 6.52 g (85.75 mmol) of 1-hydroxyurea are added. A solution of 7.13 g (178.09 mmol) of NaOH in 15 ml of water is then slowly added dropwise at 0° C., and the mixture is boiled under reflux for 3.5 hours. The solvents are concentrated and the residue is then dissolved in 20 ml of water and extracted three times with in each case 10 ml of dichloromethane. The combined organic phases are dried over sodium sulfate and concentrated. Yield: 2.8 g (29%).

1H-NMR, DMSO-$d_6$, 400 MHz: 8.24 (s, 1H), 5.56 (bs, 2H), 2.71 (t, 2H), 2.60 (t, 2H).

Synthesis of 2-chloro-N-(4-methyl-1,2-oxazol-3-yl)-4-(methylsulfonyl)-3-[(2,2,2-trifluoroethoxy)methyl]benzamide (Table Example No. 2-334)

200 mg (0.58 mmol) of 2-chloro-4-(methylsulfonyl)-3-[(2,2,2-trifluoroethoxy)methyl]benzoic acid and 57 mg (0.58 mmol) of 4-methyl-1,2-oxazole-3-amine are dissolved at RT in 24 ml of $CH_2Cl_2$, and 0.08 ml (0.58 mmol) of triethylamine, 14 mg (0.12 mmol) of DMAP and 0.55 g (0.86 mmol) of 2,4,6-tripropyl-1,3,5,2,4,6-trioxatriphosphinane 2,4,6-trioxide (50% solution in THF) are added. The reaction mixture is stirred at RT for 20 h and then washed twice with in each case 10 ml of water. The organic phase is dried over $Na_2SO_4$ and concentrated. The residue is purified by column chromatography (silica gel, heptane/ethyl acetate). Yield 150 mg (55%).

$^1$H-NMR, $CDCl_3$, 400 MHz: 8.56 (bs, 1H), 8.17 (s, 1H), 8.13 (d, 1H), 7.79 (d, 1H), 5.36 (s, 2H), 4.08 (q, 2H), 3.21 (s, 3H), 2.12 (s, 3H).

Synthesis of 4-methyl-1,2-oxazole-3-amine

At 0° C., 4.05 g (25.34 mmol) of bromine are slowly added dropwise to a solution of 2.0 g (29.81 mmol) of methacrylonitrile. The mixture is then stirred at 35° C. for 2 h. The mixture is then once more cooled to 0° C., and 2.95 g (38.75 mmol) of 1-hydroxyurea are added. A solution of 3.22 g (80.49 mmol) of NaOH in 4 ml of water is then slowly added dropwise at 0° C., and the mixture is boiled under reflux for 3.5 hours. The solvents are concentrated and the residue is then dissolved in 20 ml of water and extracted three times with in each case 10 ml of dichloromethane. The combined organic phases are dried over sodium sulfate, concentrated and purified on silica gel (heptane/ethyl acetate). Yield: 0.7 g (24%).

$^1$H-NMR, DMSO-$d_6$, 400 MHz: 7.85 (s, 1H), 3.39 (bs, 2H), 1.92 (s, 3H).

2-Methyl-3-(methylsulfonyl)-4-(trifluoromethyl)-N-[4-(trifluoromethyl)-1,2-oxazol-3-yl]benzamide (Table Example 7-173)

At 0° C., 129 mg (1.063 mmol) of thionyl chloride are added to a solution of 162 mg (1.063 mmol) of 4-(trifluoromethyl)-1,2-oxazole-3-amine and 200 mg of 2-methyl-3-methylsulfonyl-4-trifluoromethylbenzoic acid in 4 ml of pyridine. The reaction mixture is stirred at 0° C. for 1 h and then overnight at room temperature. The mixture is then concentrated. The residue is then dissolved in 5 ml of dichloromethane and extracted three times with in each case 5 ml of water. The combined organic phases are dried over magnesium sulfate, filtered and concentrated. The residue is purified by column chromatography (HPLC, acetonitrile/water). Yield 233 mg (57%).

$^1$H-NMR, DMSO-$d_6$, 400 MHz: 11.48 (s, 1H), 9.85 (s, 1H), 8.04 (d, 1H), 7.90 (d, 1H), 3.43 (s, 3H), 2.73 (s, 3H)

Synthesis of 4-(trifluoromethyl)-1,2-oxazole-3-amine

1st Stage: Synthesis of 2-bromo-2-(bromomethyl)-3,3,3-trifluoropropanonitrile To a solution of 30.4 g (190 mmol) of bromine in 100 ml of abs. chloroform are slowly added dropwise with stirring at 5° C. 23 g (190 mmol) of 2-(trifluoromethyl)acrylonitrile. The reaction mixture is then irradiated with a conventional laboratory lamp for 6 h. The red solution is then concentrated. The residue (red oil, 43 g (81%) is used further in the next step, without further purification.

2nd Stage: Synthesis of 4-(trifluoromethyl)-1,2-oxazole-3-amine

At 5° C., 15 g (195 mmol) of 1-hydroxyurea are added to a solution of 42 g (150 mmol) of 2-bromo-2-(bromomethyl)-3,3,3-trifluoropropanonitrile in 120 ml of methanol. A 50% strength aqueous sodium hydroxide solution (31 g; 0.39 mmol of NaOH) is then slowly added dropwise. After 4 hours of stirring under reflux, the brown solution is poured onto 200 ml of water and extracted three times with in each case 50 ml of ethyl acetate. The combined organic phases are washed with 20 ml of water, dried over magnesium sulfate and concentrated. The residue is distilled under reduced pressure (b.p.: 50-55° C., 1 Torr) and then purified by column chromatography (silica gel, methanol:chloroform 100:1). Yield: 4.4 g (19%)

$^1$H-NMR, $CDCl_3$: 8.41 (s, 1H); 4.2 (bs, 2H)
$^{19}$F-NMR, $CFCl_3$, $CDCl_3$: −59.24 (s)

The compound 4-(trifluoromethyl)-1,2-oxazole-3-amine is novel and also forms part of the subject matter of the present invention.

The examples listed in the tables below were prepared analogously to the abovementioned methods or are obtainable analogously to the abovementioned methods. The compounds listed in the tables below are very particularly preferred.

The abbreviations and terms used denote:
Et=ethyl Me=methyl n-Pr=n-propyl i-Pr=isopropyl
c-Pr=cyclopropyl Ph=phenyl Ac=acetyl t-Bu=tert-butyl

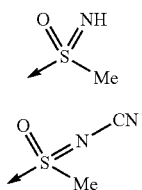
Sulfoximine 1

Sulfoximine 2

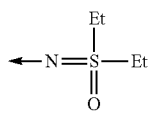
Sulfoximine 3

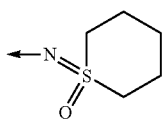
Sulfoximine 4

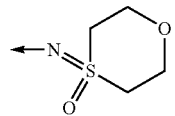
Sulfoximine 5

TABLE 1

Compounds of the general formula (I) according to the invention in which R respresents H and A represents C—Y.

(I)

| No. | X | Y | Z | V | Physical data ($^1$H-NMR, DMSO-$d_6$, 400 MHz) |
|---|---|---|---|---|---|
| 1-1 | F | H | F | H | 11.49 (s, 1H), 8.87 (s, 1H), 7.79 (ddd, 1H), 7.42 (td, 1H), 7.22 (td, 1H), 7.01 (s, 1H). |
| 1-2 | F | H | Cl | H | |
| 1-3 | F | H | SO$_2$Me | H | |
| 1-4 | F | H | SO$_2$Et | H | |
| 1-5 | F | H | CF$_3$ | H | |
| 1-6 | F | H | NO$_2$ | H | |
| 1-7 | Cl | H | F | H | |
| 1-8 | Cl | H | F | F | |
| 1-9 | Cl | H | Cl | H | 11.70 (s, 1H), 8.87 (s, 1H), 7.78 (s, 1H), 7.78 (d, 1H), 7.56 (d, 1H), 7.02 (s, 1H), |
| 1-10 | Cl | H | Br | H | |
| 1-11 | Cl | H | SMe | H | |
| 1-12 | Cl | H | SOMe | H | |
| 1-13 | Cl | H | SO$_2$Me | H | 11.84 (s, 1H), 8.89 (s, 1H), 8.11 (d, 1H), 7.99 (dd, 1H), 7.89 (dd, 1H), 3.37 (s, 3H), |
| 1-14 | Cl | H | SO$_2$Et | H | |
| 1-15 | Cl | H | CF$_3$ | H | |
| 1-16 | Cl | H | NO$_2$ | H | |
| 1-17 | Cl | H | pyrazol-1-yl | H | |
| 1-18 | Br | H | Cl | H | |
| 1-19 | Br | H | Br | H | |
| 1-20 | Br | H | SO$_2$Me | H | |
| 1-21 | Br | H | SO$_2$Et | H | |
| 1-22 | Br | H | CF$_3$ | H | |
| 1-23 | SO$_2$Me | H | Cl | H | |
| 1-24 | SO$_2$Me | H | Br | H | |
| 1-25 | SO$_2$Me | H | SMe | H | |
| 1-26 | SO$_2$Me | H | SOMe | H | |
| 1-27 | SO$_2$Me | H | SO$_2$Me | H | |
| 1-28 | SO$_2$Me | H | SO$_2$Et | H | |
| 1-29 | SO$_2$Me | H | CF$_3$ | H | 11.90 (s, 1H), 8.27 (d, 1H), 8.26 (s, 1H), 8.02 d, 1H), |

TABLE 1-continued

Compounds of the general formula (I) according to the invention in which R respresents H and A represents C—Y.

(I)

| No. | X | Y | Z | V | Physical data ($^1$H-NMR, DMSO-$d_6$, 400 MHz) |
|---|---|---|---|---|---|
| 1-30 | SO$_2$Et | H | Cl | H | 7.01 (d, 1H), 3.45 (s, 3H). |
| 1-31 | SO$_2$Et | H | Br | H | |
| 1-32 | SO$_2$Et | H | SMe | H | |
| 1-33 | SO$_2$Et | H | SO$_2$Me | H | |
| 1-34 | SO$_2$Et | H | CF$_3$ | H | |
| 1-35 | CH$_2$SO$_2$Me | H | Br | H | 11.60 (s, 1H), 8.84 (d, 1H), 7.79 (d, 1H), 7.75 (dd, 1H), 7.65 (dd, 1H), 6.99 (d, 1H), 2.33 (d, 3H), 4.85 (s, 2H), 2.94 (s, 3H) |
| 1-36 | CH$_2$SO$_2$Me | H | CF$_3$ | H | 11.75 (s, 1H), 8.86 (d, 1H), 7.95 (s, 1H), 7.91 (s, 2H), 7.02 (d, 1H), 4.94 (d, 3H), 2.97 (s, 3H) |
| 1-37 | NO$_2$ | H | F | H | |
| 1-38 | NO$_2$ | H | Cl | H | |
| 1-39 | NO$_2$ | H | Br | H | |
| 1-40 | NO$_2$ | H | I | H | |
| 1-41 | NO$_2$ | H | CN | H | |
| 1-42 | NO$_2$ | H | SO$_2$Me | H | 11.95 (s, 1H), 8.91 (d, 1H), 8.63 (d, 1H), 8.41 (dd, 1H), 8.09 (d, 1H), 7.03 (d, 1H), 3.42 (s, 3H) |
| 1-43 | NO$_2$ | H | SO$_2$Et | H | |
| 1-44 | NO$_2$ | H | CF$_3$ | H | |
| 1-45 | Me | H | F | H | |
| 1-46 | Me | H | Cl | H | |
| 1-47 | Me | H | Br | H | |
| 1-48 | Me | H | I | H | |
| 1-49 | Me | H | CN | H | |
| 1-50 | Me | H | SO$_2$Me | H | |
| 1-51 | Me | H | SO$_2$Et | H | |
| 1-52 | Me | H | CF$_3$ | H | |
| 1-53 | Et | H | F | H | |
| 1-54 | Et | H | Cl | H | |
| 1-55 | Et | H | Br | H | |
| 1-56 | Et | H | I | H | |
| 1-57 | Et | H | CN | H | |
| 1-58 | Et | H | SO$_2$Me | H | |
| 1-59 | Et | H | SO$_2$Et | H | |
| 1-60 | Et | H | CF$_3$ | H | |
| 1-61 | CF$_3$ | H | NO$_2$ | H | |
| 1-62 | CF$_3$ | H | Br | H | |
| 1-63 | CF$_3$ | H | CF$_3$ | H | |
| 1-64 | CF$_3$ | H | SO$_2$Me | H | |
| 1-65 | CF$_3$ | H | SO$_2$Et | H | |
| 1-66 | CF$_3$ | H | Cl | H | |
| 1-67 | NO$_2$ | NH$_2$ | F | H | |
| 1-68 | NO$_2$ | NHMe | F | H | |
| 1-69 | NO$_2$ | NMe$_2$ | F | H | |
| 1-70 | NO$_2$ | Me | Cl | H | |
| 1-71 | NO$_2$ | NH$_2$ | Cl | H | |
| 1-72 | NO$_2$ | NHMe | Cl | H | |
| 1-73 | NO$_2$ | NMe$_2$ | Cl | H | |
| 1-74 | NO$_2$ | NH$_2$ | Br | H | |
| 1-75 | NO$_2$ | NHMe | Br | H | |
| 1-76 | NO$_2$ | NMe$_2$ | Br | H | |
| 1-77 | NO$_2$ | NH$_2$ | CF$_3$ | H | |
| 1-78 | NO$_2$ | NMe$_2$ | CF$_3$ | H | |
| 1-79 | NO$_2$ | NH$_2$ | SO$_2$Me | H | |

TABLE 1-continued

Compounds of the general formula (I) according to the invention in which R respresents H and A represents C—Y.

(I)

| No. | X | Y | Z | V | Physical data (¹H-NMR, DMSO-$d_6$, 400 MHz) |
|---|---|---|---|---|---|
| 1-80 | $NO_2$ | $NH_2$ | $SO_2Et$ | H | |
| 1-81 | $NO_2$ | NHMe | $SO_2Me$ | H | |
| 1-82 | $NO_2$ | $NMe_2$ | $SO_2Me$ | H | |
| 1-83 | $NO_2$ | $NMe_2$ | $SO_2Et$ | H | |
| 1-84 | $NO_2$ | $NH_2$ | 1H-1,2,4-triazol-1-yl | H | |
| 1-85 | $NO_2$ | NHMe | 1H-1,2,4-triazol-1-yl | H | |
| 1-86 | $NO_2$ | $NMe_2$ | 1H-1,2,4-triazol-1-yl | H | |
| 1-87 | Me | F | F | H | |
| 1-88 | Me | F | Cl | H | |
| 1-89 | Me | Me | $SO_2Me$ | H | 11.58 (s, 1H), 8.87 (d, 1H), 7.88 (d, 1H), 7.52 d, 1H), 7.05 (d, 1H), 3.31 (s, 3H), 2.62 (s, 3H), 2.32 (s, 3H) |
| 1-90 | Me | F | $SO_2Me$ | H | 11.70 (s, 1H), 8.88 (s, 1H), 8.65 (s, 1H), 7.79 (t, 1H), 7.48 (d, 1H), 2.33 (d, 3H), |
| 1-91 | Me | Cl | Cl | H | |
| 1-92 | Me | $O(CH_2)_2OMe$ | Cl | H | |
| 1-93 | Me | $O(CH_2)_3OMe$ | Cl | H | |
| 1-94 | Me | $O(CH_2)_4OMe$ | Cl | H | |
| 1-95 | Me | $OCH_2CONMe_2$ | Cl | H | |
| 1-96 | Me | $O(CH_2)_2$—CO—$NMe_2$ | Cl | H | |
| 1-97 | Me | $O(CH_2)_2$—NH(CO)$NMe_2$ | Cl | H | |
| 1-98 | Me | $O(CH_2)_2$—NH(CO)NHCO$_2$Et | Cl | H | |
| 1-99 | Me | $O(CH_2)_2$—NHCO$_2$Me | Cl | H | |
| 1-100 | Me | $OCH_2$—NHSO$_2$cPr | Cl | H | |
| 1-101 | Me | $O(CH_2)$-5-2,4-dimethyl-2,4-dihydro-3H-1,2,4-triazol-3-one | Cl | H | |
| 1-102 | Me | $O(CH_2)$-3,5-dimethyl-1,2-oxazol-4-yl | Cl | H | |
| 1-103 | Me | $OCH_2(CO)NMe_2$ | Br | H | |
| 1-104 | Me | $O(CH_2)$-5-pyrrolidin-2-one | Br | H | |
| 1-105 | Me | Cl | $CF_3$ | H | |
| 1-106 | Me | Me | $SO_2Me$ | H | |
| 1-107 | Me | 4,5-dihydro-1,2-oxazol-3-yl | $SO_2Me$ | H | |
| 1-108 | Me | 4,5-dihydro-1,2-oxazol-3-yl | $SO_2Et$ | H | |
| 1-109 | Me | 5-cyanomethyl-4,5-dihydro-1,2-oxazol-3-yl | $SO_2Me$ | H | |
| 1-110 | Me | 5-cyanomethyl-4,5-dihydro-1,2-oxazol-3-yl | $SO_2Et$ | H | |
| 1-111 | Me | $NHCH_2C(O)NMe_2$ | $SO_2Me$ | H | |
| 1-112 | Me | SMe | Me | H | |
| 1-113 | Me | SOMe | Me | H | |
| 1-114 | Me | $SO_2Me$ | Me | H | |
| 1-115 | Me | SEt | Me | H | |
| 1-116 | Me | SOEt | Me | H | |
| 1-117 | Me | $SO_2Et$ | Me | H | |
| 1-118 | Me | $S(CH_2)_2OMe$ | Me | H | |
| 1-119 | Me | $SO(CH_2)_2OMe$ | Me | H | |
| 1-120 | Me | $SO_2(CH_2)_2OMe$ | Me | H | |
| 1-121 | Me | $SO_2cPr$ | Me | H | |
| 1-122 | Me | OH | $SO_2Me$ | H | |
| 1-123 | Me | OMe | $SO_2Me$ | H | |
| 1-124 | Me | OMe | $SO_2Et$ | H | |

TABLE 1-continued

Compounds of the general formula (I) according to the invention in which R respresents H and A represents C—Y.

(I)

| No. | X | Y | Z | V | Physical data ($^1$H-NMR, DMSO-$d_6$, 400 MHz) |
|---|---|---|---|---|---|
| 1-125 | Me | OEt | SO$_2$Me | H | |
| 1-126 | Me | OEt | SO$_2$Et | H | |
| 1-127 | Me | OiPr | SO$_2$Me | H | |
| 1-128 | Me | OiPr | SO$_2$Et | H | |
| 1-129 | Me | O(CH$_2$)$_2$OMe | SO$_2$Me | H | |
| 1-130 | Me | O(CH$_2$)$_2$OMe | SO$_2$Et | H | |
| 1-131 | Me | O(CH$_2$)$_3$OMe | SO$_2$Me | H | |
| 1-132 | Me | O(CH$_2$)$_3$OMe | SO$_2$Et | H | |
| 1-133 | Me | O(CH$_2$)$_4$OMe | SO$_2$Me | H | |
| 1-134 | Me | O(CH$_2$)$_4$OMe | SO$_2$Et | H | |
| 1-135 | Me | O(CH$_2$)$_2$NHSO$_2$Me | SO$_2$Me | H | |
| 1-136 | Me | O(CH$_2$)$_2$NHSO$_2$Me | SO$_2$Et | H | |
| 1-137 | Me | OCH$_2$(CO)NMe$_2$ | SO$_2$Me | H | |
| 1-138 | Me | OCH$_2$(CO)NMe$_2$ | SO$_2$Et | H | |
| 1-139 | Me | [1,4]dioxan-2-yl-methoxy | SO$_2$Me | H | |
| 1-140 | Me | [1,4]dioxan-2-yl-methoxy | SO$_2$Et | H | |
| 1-141 | Me | O(CH$_2$)$_2$—O-(3,5-di-methoxypyrimidin-2-yl) | SO$_2$Me | H | |
| 1-142 | Me | Cl | SO$_2$Me | H | 11.72 (s, 1H), 8.89 (d, 1H), 8.01 (d, 1H), 7.72 d, 1H), 7.05 (d, 1H), 3.43 (s, 3H), 2.44 (s, 3H) |
| 1-143 | Me | SMe | H | H | |
| 1-144 | Me | SOMe | H | H | |
| 1-145 | Me | SO$_2$Me | H | H | |
| 1-146 | Me | SEt | H | H | |
| 1-147 | Me | SOEt | H | H | |
| 1-148 | Me | SO$_2$Et | H | H | |
| 1-149 | Me | S(CH$_2$)$_2$OMe | H | H | |
| 1-150 | Me | SO(CH$_2$)$_2$OMe | H | H | |
| 1-151 | Me | SO$_2$(CH$_2$)$_2$OMe | H | H | |
| 1-152 | Me | SMe | F | H | |
| 1-153 | Me | SOMe | F | H | |
| 1-154 | Me | SO$_2$Me | F | H | |
| 1-155 | Me | SEt | F | H | |
| 1-156 | Me | SOEt | F | H | |
| 1-157 | Me | SO$_2$Et | F | H | |
| 1-158 | Me | S(CH$_2$)$_2$OMe | F | H | |
| 1-159 | Me | SO(CH$_2$)$_2$OMe | F | H | |
| 1-160 | Me | SO$_2$(CH$_2$)$_2$OMe | F | H | |
| 1-161 | Me | SMe | SO$_2$Me | H | |
| 1-162 | Me | SOMe | SO$_2$Me | H | |
| 1-163 | Me | SO$_2$Me | SO$_2$Me | H | 11.79 (s, 1H), 8.91 (d, 1H), 8.22 (d, 1H), 8.03 d, 1H), 7.06 (d, 1H), 3.60 (s, 3H), 3.56 (s, 3H), 2.67 (s, 3H) |
| 1-164 | Me | SO$_2$Me | SO$_2$Et | H | |
| 1-165 | Me | SEt | SO$_2$Me | H | |
| 1-166 | Me | SOEt | SO$_2$Me | H | |
| 1-167 | Me | SO$_2$Et | SO$_2$Me | H | |
| 1-168 | Me | S(CH$_2$)$_2$OMe | SO$_2$Me | H | |
| 1-169 | Me | SO(CH$_2$)$_2$OMe | SO$_2$Me | H | |
| 1-170 | Me | SO$_2$(CH$_2$)$_2$OMe | SO$_2$Me | H | |
| 1-171 | Me | SMe | CF$_3$ | H | 11.60 (s, 1H), 8.89 (d, 1H), 7.76 (d, 1H), 7.66 (d, 1H), 7.06 (d, 1H), 2.64 (s, 3H), 2.31 (s, 3H) |
| 1-172 | Me | SOMe | CF$_3$ | H | 11.70 (s, 1H), 8.89 (d, 1H), 7.84 (d, 1H), 7.80 (d, 1H), |

TABLE 1-continued

Compounds of the general formula (I) according to the invention in which R respresents H and A represents C—Y.

(I)

| No. | X | Y | Z | V | Physical data ($^1$H-NMR, DMSO-$d_6$, 400 MHz) |
|---|---|---|---|---|---|
| | | | | | 7.06 (d, 1H), 3.04 (s, 3H), 2.82 (s, 3H) |
| 1-173 | Me | SO$_2$Me | CF$_3$ | H | 11.76 (s, 1H), 8.90 (d, 1H), 8.00 (d, 1H), 7.95 d, 1H), 7.06 (d, 1H), 3.41 (s, 3H), 2.70 (s, 3H) |
| 1-174 | Me | SEt | CF$_3$ | H | |
| 1-175 | Me | SOEt | CF$_3$ | H | |
| 1-176 | Me | SO$_2$Et | CF$_3$ | H | |
| 1-177 | Me | S(CH$_2$)$_2$OMe | CF$_3$ | H | |
| 1-178 | Me | SO(CH$_2$)$_2$OMe | CF$_3$ | H | |
| 1-179 | Me | SO$_2$(CH$_2$)$_2$OMe | CF$_3$ | H | |
| 1-180 | Me | SMe | Br | H | |
| 1-181 | Me | SOMe | Br | H | |
| 1-182 | Me | SO$_2$Me | Br | H | |
| 1-183 | Me | SEt | Br | H | |
| 1-184 | Me | SOEt | Br | H | |
| 1-185 | Me | SO$_2$Et | Br | H | |
| 1-186 | Me | SMe | I | H | |
| 1-187 | Me | SOMe | I | H | |
| 1-188 | Me | SO$_2$Me | I | H | |
| 1-189 | Me | SEt | I | H | |
| 1-190 | Me | SOEt | I | H | |
| 1-191 | Me | SO$_2$Et | I | H | |
| 1-192 | Me | SMe | Cl | H | |
| 1-193 | Me | SOMe | Cl | H | |
| 1-194 | Me | SO$_2$Me | Cl | H | |
| 1-195 | Me | SEt | Cl | H | |
| 1-196 | Me | SOEt | Cl | H | |
| 1-197 | Me | SO$_2$Et | Cl | H | |
| 1-198 | Me | S(CH$_2$)$_2$OMe | Cl | H | |
| 1-199 | Me | SO(CH$_2$)$_2$OMe | Cl | H | |
| 1-200 | Me | SO$_2$(CH$_2$)$_2$OMe | Cl | H | |
| 1-201 | CH$_2$SMe | OMe | SO$_2$Me | H | |
| 1-202 | CH$_2$OMe | OMe | SO$_2$Me | H | |
| 1-203 | CH$_2$O(CH$_2$)$_2$OMe | NH(CH$_2$)$_2$OEt | SO$_2$Me | H | |
| 1-204 | CH$_2$O(CH$_2$)$_2$OMe | NH(CH$_2$)$_3$OEt | SO$_2$Me | H | |
| 1-205 | CH$_2$O(CH$_2$)$_3$OMe | OMe | SO$_2$Me | H | |
| 1-206 | CH$_2$O(CH$_2$)$_2$OMe | NH(CH$_2$)$_2$OMe | SO$_2$Me | H | |
| 1-207 | CH$_2$O(CH$_2$)$_2$OMe | NH(CH$_2$)$_3$OMe | SO$_2$Me | H | |
| 1-208 | Et | SMe | Cl | H | |
| 1-209 | Et | SOMe | Cl | H | |
| 1-210 | Et | SO$_2$Me | Cl | H | |
| 1-211 | Et | SMe | CF$_3$ | H | |
| 1-212 | Et | SOMe | CF$_3$ | H | |
| 1-213 | Et | SO$_2$Me | CF$_3$ | H | |
| 1-214 | Et | F | SO$_2$Me | H | 11.77 (s, 1H), 8.89 (d, 1H), 7.81 (dd, 1H), 7.59 d, 1H), 7.05 (d, 1H), 3.44 (s, 3H), 2.77 (q, 2H), 1.18 (t, 3H). |
| 1-215 | Et | NH(CH$_2$)$_2$OMe | SO$_2$Me | H | |
| 1-216 | iPr | SMe | CF$_3$ | H | |
| 1-217 | iPr | SOMe | CF$_3$ | H | |
| 1-218 | iPr | SO$_2$Me | CF$_3$ | H | |
| 1-219 | cPr | SMe | CF$_3$ | H | |
| 1-220 | cPr | SOMe | CF$_3$ | H | |
| 1-221 | cPr | SO$_2$Me | CF$_3$ | H | |
| 1-222 | CF$_3$ | O(CH$_2$)$_2$OMe | F | H | |
| 1-223 | CF$_3$ | O(CH$_2$)$_3$OMe | F | H | |
| 1-224 | CF$_3$ | OCH$_2$CONMe$_2$ | F | H | |

TABLE 1-continued

Compounds of the general formula (I) according to the invention in which R respresents H and A represents C—Y.

| No. | X | Y | Z | V | Physical data ($^1$H-NMR, DMSO-$d_6$, 400 MHz) |
|---|---|---|---|---|---|
| 1-225 | $CF_3$ | [1,4]dioxan-2-yl-methoxy | F | H | |
| 1-226 | $CF_3$ | $O(CH_2)_2OMe$ | Cl | H | |
| 1-227 | $CF_3$ | $O(CH_2)_3OMe$ | Cl | H | |
| 1-228 | $CF_3$ | $OCH_2CONMe_2$ | Cl | H | |
| 1-229 | $CF_3$ | [1,4]dioxan-2-ylmethoxy | Cl | H | |
| 1-230 | $CF_3$ | $O(CH_2)_2OMe$ | Br | H | |
| 1-231 | $CF_3$ | $O(CH_2)_3OMe$ | Br | H | |
| 1-232 | $CF_3$ | $OCH_2CONMe_2$ | Br | H | |
| 1-233 | $CF_3$ | [1,4]dioxan-2-ylmethoxy | Br | H | |
| 1-234 | $CF_3$ | $O(CH_2)_2OMe$ | I | H | |
| 1-235 | $CF_3$ | $O(CH_2)_3OMe$ | I | H | |
| 1-236 | $CF_3$ | $OCH_2CONMe_2$ | I | H | |
| 1-237 | $CF_3$ | [1,4]dioxan-2-ylmethoxy | I | H | |
| 1-238 | $CF_3$ | F | $SO_2Me$ | H | |
| 1-239 | $CF_3$ | F | $SO_2Et$ | H | |
| 1-240 | $CF_3$ | $O(CH_2)_2OMe$ | $SO_2Me$ | H | |
| 1-241 | $CF_3$ | $O(CH_2)_2OMe$ | $SO_2Et$ | H | |
| 1-242 | $CF_3$ | $O(CH_2)_3OMe$ | $SO_2Me$ | H | |
| 1-243 | $CF_3$ | $O(CH_2)_3OMe$ | $SO_2Et$ | H | |
| 1-244 | $CF_3$ | $OCH_2CONMe_2$ | $SO_2Me$ | H | |
| 1-245 | $CF_3$ | $OCH_2CONMe_2$ | $SO_2Et$ | H | |
| 1-246 | $CF_3$ | [1,4]dioxan-2-ylmethoxy | $SO_2Me$ | H | |
| 1-247 | $CF_3$ | [1,4]dioxan-2-ylmethoxy | $SO_2Et$ | H | |
| 1-248 | F | SMe | $CF_3$ | H | 11.78 (s, 1H), 8.87 (s, 1H), 7.81 (t, 1H), 7.73 (d, 1H), 7.02 (s, 1H), 2.50 (s, 3H) |
| 1-249 | F | SOMe | $CF_3$ | H | |
| 1-250 | Cl | Me | $SO_2Et$ | H | 11.75 (s, 1H), 8.89 (d, 1H), 7.97 (d, 1H), 7.70 d, 1H), 7.04 (d, 1H), 3.40 (q, 2H), 2.73 (s, 3H), 1.13 (t, 3H) |
| 1-251 | Cl | $OCH_2CHCH_2$ | Cl | H | |
| 1-252 | Cl | $OCH_2CHF_2$ | Cl | H | |
| 1-253 | Cl | $O(CH_2)_2OMe$ | Cl | H | |
| 1-254 | Cl | $OCH_2CONMe_2$ | Cl | H | 11.69 (s, 1H), 8.88 (d, 1H), 7.62 (d, 1H), 7.43 d, 1H), 7.02 (d, 1H), 4.72 (s, 2H), 3.01 (s, 3H), 2.87 (s, 3H) |
| 1-255 | Cl | $O(CH_2)$-5-pyrrolidin-2-one | Cl | H | |
| 1-256 | Cl | SMe | H | H | |
| 1-257 | Cl | SOMe | H | H | |
| 1-258 | Cl | $SO_2Me$ | H | H | |
| 1-259 | Cl | SEt | H | H | |
| 1-260 | Cl | SOEt | H | H | |
| 1-261 | Cl | $SO_2Et$ | H | H | |
| 1-262 | Cl | $S(CH_2)_2OMe$ | H | H | |
| 1-263 | Cl | $SO(CH_2)_2OMe$ | H | H | |
| 1-264 | Cl | $SO_2(CH_2)_2OMe$ | H | H | |
| 1-265 | Cl | SMe | Me | H | |
| 1-266 | Cl | SOMe | Me | H | |
| 1-267 | Cl | $SO_2Me$ | Me | H | |
| 1-268 | Cl | SEt | Me | H | |
| 1-269 | Cl | SOEt | Me | H | |
| 1-270 | Cl | $SO_2Et$ | Me | H | |

TABLE 1-continued

Compounds of the general formula (I) according to the invention in which R respresents H and A represents C—Y.

(I)

| No. | X | Y | Z | V | Physical data ($^1$H-NMR, DMSO-$d_6$, 400 MHz) |
|---|---|---|---|---|---|
| 1-271 | Cl | S(CH$_2$)$_2$OMe | Me | H | |
| 1-272 | Cl | SO(CH$_2$)$_2$OMe | Me | H | |
| 1-273 | Cl | SO$_2$(CH$_2$)$_2$OMe | Me | H | |
| 1-274 | Cl | SMe | F | H | |
| 1-275 | Cl | SOMe | F | H | |
| 1-276 | Cl | SO$_2$Me | F | H | |
| 1-277 | Cl | SEt | F | H | |
| 1-278 | Cl | SOEt | F | H | |
| 1-279 | Cl | SO$_2$Et | F | H | |
| 1-280 | Cl | S(CH$_2$)$_2$OMe | F | H | |
| 1-281 | Cl | SO(CH$_2$)$_2$OMe | F | H | |
| 1-282 | Cl | SO$_2$(CH$_2$)$_2$OMe | F | H | |
| 1-283 | Cl | SMe | SO$_2$Me | H | 11.79 (s, 1H), 8.86 (s, 1H), 8.07 (d, 1H), 7.84 (d, 1H), 7.04 (s, 1H), 3.57 (s, 3H), 3.50 (s, 3H) |
| 1-284 | Cl | SOMe | SO$_2$Me | H | 11.88 (s, 1H), 8.92 (s, 1H), 8.10 (d, 1H), 8.01 (d, 1H), 7.06 (s, 1H), 3.54 (s, 3H), 3.19 (s, 3H) |
| 1-285 | Cl | SO$_2$Me | SO$_2$Me | H | 11.91 (s, 1H), 8.92 (s, 1H), 8.33 (d, 1H), 8.18 (d, 1H), 7.06 (s, 1H), 3.66 (s, 3H), 3.56 (s, 3H) |
| 1-286 | Cl | SO$_2$Me | SO$_2$Et | H | |
| 1-287 | Cl | SEt | SO$_2$Me | H | |
| 1-288 | Cl | SOEt | SO$_2$Me | H | |
| 1-289 | Cl | SO$_2$Et | SO$_2$Me | H | |
| 1-290 | Cl | S(CH$_2$)$_2$OMe | SO$_2$Me | H | |
| 1-291 | Cl | SO(CH$_2$)$_2$OMe | SO$_2$Me | H | |
| 1-292 | Cl | SO$_2$(CH$_2$)$_2$OMe | SO$_2$Me | H | |
| 1-293 | Cl | SMe | CF$_3$ | H | 11.78 (s, 1H), 8.90 (s, 1H), 7.91 (d, 1H), 7.88 (d, 1H), 7.05 (s, 1H), 2.44 (s, 3H) |
| 1-294 | Cl | SOMe | CF$_3$ | H | 11.87 (s, 1H), 8.92 (s, 1H), 8.02 (d, 1H), 7.98 (d, 1H), 7.06 (s, 1H), 3.15 (s, 3H) |
| 1-295 | Cl | SO$_2$Me | CF$_3$ | H | 11.91 (s, 1H), 8.92 (s, 1H), 8.16 (d, 1H), 8.13 (d, 1H), 7.06 (s, 1H), 3.52 (s, 3H) |
| 1-296 | Cl | SEt | CF$_3$ | H | |
| 1-297 | Cl | SOEt | CF$_3$ | H | |
| 1-298 | Cl | SO$_2$Et | CF$_3$ | H | |
| 1-299 | Cl | S(CH$_2$)$_2$OMe | CF$_3$ | H | |
| 1-300 | Cl | SO(CH$_2$)$_2$OMe | CF$_3$ | H | |
| 1-301 | Cl | SO$_2$(CH$_2$)$_2$OMe | CF$_3$ | H | |
| 1-302 | Cl | SMe | Br | H | |
| 1-303 | Cl | SOMe | Br | H | |
| 1-304 | Cl | SO$_2$Me | Br | H | |
| 1-305 | Cl | SEt | Br | H | |
| 1-306 | Cl | SOEt | Br | H | |
| 1-307 | Cl | SO$_2$Et | Br | H | |
| 1-308 | Cl | SMe | I | H | |
| 1-309 | Cl | SOMe | I | H | |
| 1-310 | Cl | SO$_2$Me | I | H | |
| 1-311 | Cl | SEt | I | H | |
| 1-312 | Cl | SOEt | I | H | |
| 1-313 | Cl | SO$_2$Et | I | H | |
| 1-314 | Cl | SMe | Cl | H | |
| 1-315 | Cl | SOMe | Cl | H | |
| 1-316 | Cl | SO$_2$Me | Cl | H | |

TABLE 1-continued

Compounds of the general formula (I) according to the invention in which R respresents H and A represents C—Y.

(I)

| No. | X | Y | Z | V | Physical data ($^1$H-NMR, DMSO-$d_6$, 400 MHz) |
|---|---|---|---|---|---|
| 1-317 | Cl | SEt | Cl | H | |
| 1-318 | Cl | SOEt | Cl | H | |
| 1-319 | Cl | SO$_2$Et | Cl | H | |
| 1-320 | Cl | S(CH$_2$)$_2$OMe | Cl | H | |
| 1-321 | Cl | SO(CH$_2$)$_2$OMe | Cl | H | |
| 1-322 | Cl | SO$_2$(CH$_2$)$_2$OMe | Cl | H | |
| 1-323 | Cl | F | SMe | H | |
| 1-324 | Cl | Cl | SO$_2$Me | H | 11.86 (s, 1H), 8.91 (d, 1H), 8.12 (d, 1H), 7.88 d, 1H), 7.05 (d, 1H), 3.47 (s, 3H) |
| 1-325 | Cl | COOMe | SO$_2$Me | H | |
| 1-326 | Cl | CONMe$_2$ | SO$_2$Me | H | |
| 1-327 | Cl | CONMe(OMe) | SO$_2$Me | H | |
| 1-328 | Cl | CH$_2$OMe | SO$_2$Me | H | |
| 1-329 | Cl | CH$_2$OMe | SO$_2$Et | H | |
| 1-330 | Cl | CH$_2$OEt | SO$_2$Me | H | |
| 1-331 | Cl | CH$_2$OEt | SO$_2$Et | H | |
| 1-332 | Cl | CH$_2$OCH$_2$CH$_2$OMe | SO$_2$Me | H | |
| 1-333 | Cl | CH$_2$OCH$_2$CHF$_2$ | SO$_2$Me | H | |
| 1-334 | Cl | CH$_2$OCH$_2$CF$_3$ | SO$_2$Me | H | 9.50 (s, 1H), 8.32 (s, 1H), 8.22 (d, 1H), 7.79 (d, 1H), 5.38 (s, 2H), 4.05 (q, 2H), 3.23 (s, 3H), 2.45 (s, 3H) |
| 1-335 | Cl | CH$_2$OCH$_2$CF$_3$ | SO$_2$Et | H | |
| 1-336 | Cl | CH$_2$OCH$_2$CF$_2$CHF$_2$ | SO$_2$Me | H | |
| 1-337 | Cl | CH$_2$OcPentyl | SO$_2$Me | H | |
| 1-338 | Cl | CH$_2$PO(OMe)$_2$ | SO$_2$Me | H | |
| 1-339 | Cl | 4,5-dihydro-1,2-oxazol-3-yl | SMe | H | |
| 1-340 | Cl | 4,5-dihydro-1,2-oxazol-3-yl | SO$_2$Me | H | |
| 1-341 | Cl | 4,5-dihydro-1,2-oxazol-3-yl | SO$_2$Et | H | |
| 1-342 | Cl | 5-cyanomethyl-4,5-dihydro-1,2-oxazol-3-yl | SO$_2$Me | H | |
| 1-343 | Cl | 5-cyanomethyl-4,5-dihydro-1,2-oxazol-3-yl | SO$_2$Et | H | 11.85 (s, 1H), 8.91 (s, 1H), 8.09 (d, 1H), 8.04 (d, 1H), 7.05 (s, 1H), 5.19 (m, 1H), 3.60 (dd, 1H), 3.42 (q, 2H), 3.14 (dd, 1H), 3.01 (m, 2H), 1.16 (t, 3H). |
| 1-344 | Cl | 5-(methoxymethyl)-4,5-dihydro-1,2-oxazol-3-yl | SO$_2$Et | H | |
| 1-345 | Cl | 5-(methoxymethyl)-5-methyl-4,5-dihydro-1,2-oxazol-3-yl | SO$_2$Et | H | |
| 1-346 | Cl | CH$_2$O-tetrahydrofuran-3-yl | SO$_2$Me | H | |
| 1-347 | Cl | CH$_2$O-tetrahydrofuran-3-yl | SO$_2$Et | H | |
| 1-348 | Cl | CH$_2$OCH$_2$-tetrahydrofuran-2-yl | SO$_2$Me | H | 11.83 (s, 1H), 8.89 (d, 1H), 8.07 (d, 1H), 7.86 d, 1H), 7.05 (d, 1H), 5.08 (s, 2H), 3.99-3.94 (m, 1H), 3.73 (q, 1H), 3.69-3.55 (m, 3H), 3.39 (s, 3H), 1.89-1.86 (m, 1H), 1.82-1.76 (m, 2H), 1.57-1.51 (m, 1H) |
| 1-349 | Cl | CH$_2$OCH$_2$-tetrahydrofuran-2-yl | SO$_2$Et | H | |

TABLE 1-continued

Compounds of the general formula (I) according to the invention in which R respresents H and A represents C—Y.

(I)

| No. | X | Y | Z | V | Physical data ($^1$H-NMR, DMSO-$d_6$, 400 MHz) |
|---|---|---|---|---|---|
| 1-350 | Cl | CH$_2$OCH$_2$-tetrahydrofuran-3-yl | SO$_2$Me | H | |
| 1-351 | Cl | CH$_2$OCH$_2$-tetrahydrofuran-3-yl | SO$_2$Et | H | |
| 1-352 | Cl | OMe | SO$_2$Me | H | |
| 1-353 | Cl | OMe | SO$_2$Et | H | |
| 1-354 | Cl | OEt | SO$_2$Me | H | |
| 1-355 | Cl | OEt | SO$_2$Et | H | |
| 1-356 | Cl | OiPr | SO$_2$Me | H | |
| 1-357 | Cl | OiPr | SO$_2$Et | H | |
| 1-358 | Cl | OnPr | SO$_2$Me | H | |
| 1-359 | Cl | O(CH$_2$)$_2$F | SO$_2$Me | H | |
| 1-360 | Cl | O(CH$_2$)$_2$OMe | SO$_2$Me | H | |
| 1-361 | Cl | O(CH$_2$)$_4$OMe | SO$_2$Me | H | |
| 1-362 | Cl | O(CH$_2$)$_4$OMe | SO$_2$Et | H | |
| 1-363 | Cl | O(CH$_2$)$_3$OMe | SO$_2$Me | H | |
| 1-364 | Cl | O(CH$_2$)$_2$OMe | SO$_2$Et | H | |
| 1-365 | Cl | O(CH$_2$)$_2$OMe | SO$_2$Me | H | |
| 1-366 | Cl | O(CH$_2$)$_2$OMe | SO$_2$Et | H | |
| 1-367 | Cl | OCH$_2$—c-Pr | SO$_2$Et | H | |
| 1-368 | Cl | [1,4]dioxan-2-yl-methoxy | SO$_2$Me | H | |
| 1-369 | Cl | [1,4]dioxan-2-yl-methoxy | SO$_2$Et | H | |
| 1-370 | Cl | OCH$_2$(CO)NMe$_2$ | SO$_2$Me | H | |
| 1-371 | Cl | OCH$_2$(CO)NMe$_2$ | SO$_2$Et | H | |
| 1-372 | Br | OMe | Br | H | |
| 1-373 | Br | O(CH$_2$)$_2$OMe | Br | H | |
| 1-374 | Br | O(CH$_2$)$_2$OMe | SO$_2$Me | H | |
| 1-375 | Br | O(CH$_2$)$_2$OMe | SO$_2$Et | H | |
| 1-376 | Br | O(CH$_2$)$_3$OMe | SO$_2$Me | H | |
| 1-377 | Br | O(CH$_2$)$_3$OMe | SO$_2$Et | H | |
| 1-378 | Br | O(CH$_2$)$_4$OMe | SO$_2$Me | H | |
| 1-379 | Br | O(CH$_2$)$_4$OMe | SO$_2$Et | H | |
| 1-380 | Br | [1,4]dioxan-2-ylmethoxy | SO$_2$Me | H | |
| 1-381 | Br | [1,4]dioxan-2-ylmethoxy | SO$_2$Et | H | |
| 1-382 | I | O(CH$_2$)$_2$OMe | SO$_2$Me | H | |
| 1-383 | I | O(CH$_2$)$_2$OMe | SO$_2$Et | H | |
| 1-384 | I | O(CH$_2$)$_3$OMe | SO$_2$Me | H | |
| 1-385 | I | O(CH$_2$)$_3$OMe | SO$_2$Et | H | |
| 1-386 | I | O(CH$_2$)$_4$OMe | SO$_2$Me | H | |
| 1-387 | I | O(CH$_2$)$_4$OMe | SO$_2$Et | H | |
| 1-388 | I | [1,4]dioxan-2-ylmethoxy | SO$_2$Me | H | |
| 1-389 | I | [1,4]dioxan-2-ylmethoxy | SO$_2$Et | H | |
| 1-390 | OMe | SMe | CF$_3$ | H | |
| 1-391 | OMe | SOMe | CF$_3$ | H | |
| 1-392 | OMe | SO$_2$Me | CF$_3$ | H | |
| 1-393 | OMe | SEt | CF$_3$ | H | |
| 1-394 | OMe | SOEt | CF$_3$ | H | |
| 1-395 | OMe | SO$_2$Et | CF$_3$ | H | |
| 1-396 | OMe | S(CH$_2$)$_2$OMe | CF$_3$ | H | |
| 1-397 | OMe | SO(CH$_2$)$_2$OMe | CF$_3$ | H | |
| 1-398 | OMe | SO$_2$(CH$_2$)$_2$OMe | CF$_3$ | H | |
| 1-399 | OMe | SMe | CHF$_2$ | H | |
| 1-400 | OMe | SOMe | CHF$_2$ | H | |
| 1-401 | OMe | SO$_2$Me | CHF$_2$ | H | |
| 1-402 | OMe | SEt | CHF$_2$ | H | |

TABLE 1-continued

Compounds of the general formula (I) according to the invention in which R respresents H and A represents C—Y.

| No. | X | Y | Z | V | Physical data ($^1$H-NMR, DMSO-$d_6$, 400 MHz) |
|---|---|---|---|---|---|
| 1-403 | OMe | SOEt | $CHF_2$ | H | |
| 1-404 | OMe | $SO_2Et$ | $CHF_2$ | H | |
| 1-405 | OMe | $S(CH_2)_2OMe$ | $CHF_2$ | H | |
| 1-406 | OMe | $SO(CH_2)_2OMe$ | $CHF_2$ | H | |
| 1-407 | OMe | $SO_2(CH_2)_2OMe$ | $CHF_2$ | H | |
| 1-408 | OMe | SMe | Cl | H | |
| 1-409 | OMe | SOMe | Cl | H | |
| 1-410 | OMe | $SO_2Me$ | Cl | H | |
| 1-411 | OMe | SEt | Cl | H | |
| 1-412 | OMe | SOEt | Cl | H | |
| 1-413 | OMe | $SO_2Et$ | Cl | H | |
| 1-414 | OMe | $S(CH_2)_2OMe$ | Cl | H | |
| 1-415 | OMe | $SO(CH_2)_2OMe$ | Cl | H | |
| 1-416 | OMe | $SO_2(CH_2)_2OMe$ | Cl | H | |
| 1-417 | OEt | SMe | $CF_3$ | H | |
| 1-418 | OEt | SOMe | $CF_3$ | H | |
| 1-419 | OEt | $SO_2Me$ | $CF_3$ | H | |
| 1-420 | OEt | SEt | $CF_3$ | H | |
| 1-421 | OEt | SOEt | $CF_3$ | H | |
| 1-422 | OEt | $SO_2Et$ | $CF_3$ | H | |
| 1-423 | OEt | $S(CH_2)_2OMe$ | $CF_3$ | H | |
| 1-424 | OEt | $SO(CH_2)_2OMe$ | $CF_3$ | H | |
| 1-425 | OEt | $SO_2(CH_2)_2OMe$ | $CF_3$ | H | |
| 1-426 | OEt | SMe | $CHF_2$ | H | |
| 1-427 | OEt | SOMe | $CHF_2$ | H | |
| 1-428 | OEt | $SO_2Me$ | $CHF_2$ | H | |
| 1-429 | OEt | SEt | $CHF_2$ | H | |
| 1-430 | OEt | SOEt | $CHF_2$ | H | |
| 1-431 | OEt | $SO_2Et$ | $CHF_2$ | H | |
| 1-432 | OEt | $S(CH_2)_2OMe$ | $CHF_2$ | H | |
| 1-433 | OEt | $SO(CH_2)_2OMe$ | $CHF_2$ | H | |
| 1-434 | OEt | $SO_2(CH_2)_2OMe$ | $CHF_2$ | H | |
| 1-435 | OEt | SMe | Cl | H | |
| 1-436 | OEt | SOMe | Cl | H | |
| 1-437 | OEt | $SO_2Me$ | Cl | H | |
| 1-438 | OEt | SEt | Cl | H | |
| 1-439 | OEt | SOEt | Cl | H | |
| 1-440 | OEt | $SO_2Et$ | Cl | H | |
| 1-441 | OEt | $S(CH_2)_2OMe$ | Cl | H | |
| 1-442 | OEt | $SO(CH_2)_2OMe$ | Cl | H | |
| 1-443 | OEt | $SO_2(CH_2)_2OMe$ | Cl | H | |
| 1-444 | $O(CH_2)$c-Pr | SMe | $CF_3$ | H | |
| 1-445 | $O(CH_2)$c-Pr | SOMe | $CF_3$ | H | |
| 1-446 | $O(CH_2)$c-Pr | $SO_2Me$ | $CF_3$ | H | |
| 1-447 | $O(CH_2)$c-Pr | SEt | $CF_3$ | H | |
| 1-448 | $O(CH_2)$c-Pr | SOEt | $CF_3$ | H | |
| 1-449 | $O(CH_2)$c-Pr | $SO_2Et$ | $CF_3$ | H | |
| 1-450 | $O(CH_2)$c-Pr | $S(CH_2)_2OMe$ | $CF_3$ | H | |
| 1-451 | $O(CH_2)$c-Pr | $SO(CH_2)_2OMe$ | $CF_3$ | H | |
| 1-452 | $O(CH_2)$c-Pr | $SO_2(CH_2)_2OMe$ | $CF_3$ | H | |
| 1-453 | $O(CH_2)$c-Pr | SMe | Cl | H | |
| 1-454 | $O(CH_2)$c-Pr | SOMe | Cl | H | |
| 1-455 | $O(CH_2)$c-Pr | $SO_2Me$ | Cl | H | |
| 1-456 | $O(CH_2)$c-Pr | SEt | Cl | H | |
| 1-457 | $O(CH_2)$c-Pr | SOEt | Cl | H | |
| 1-458 | $O(CH_2)$c-Pr | $SO_2Et$ | Cl | H | |
| 1-459 | $O(CH_2)$c-Pr | $S(CH_2)_2OMe$ | Cl | H | |
| 1-460 | $O(CH_2)$c-Pr | $SO(CH_2)_2OMe$ | Cl | H | |
| 1-461 | $O(CH_2)$c-Pr | $SO_2(CH_2)_2OMe$ | Cl | H | |
| 1-462 | $O(CH_2)$c-Pr | SMe | $SO_2Me$ | H | |
| 1-463 | $O(CH_2)$c-Pr | SOMe | $SO_2Me$ | H | |

TABLE 1-continued

Compounds of the general formula (I) according to the invention in which R respresents H and A represents C—Y.

(I)

| No. | X | Y | Z | V | Physical data ($^1$H-NMR, DMSO-$d_6$, 400 MHz) |
|---|---|---|---|---|---|
| 1-464 | O(CH$_2$)c-Pr | SO$_2$Me | SO$_2$Me | H | |
| 1-465 | O(CH$_2$)c-Pr | SEt | SO$_2$Me | H | |
| 1-466 | O(CH$_2$)c-Pr | SOEt | SO$_2$Me | H | |
| 1-467 | O(CH$_2$)c-Pr | SO$_2$Et | SO$_2$Me | H | |
| 1-468 | O(CH$_2$)c-Pr | S(CH$_2$)$_2$OMe | SO$_2$Me | H | |
| 1-469 | O(CH$_2$)c-Pr | SO(CH$_2$)$_2$OMe | SO$_2$Me | H | |
| 1-470 | O(CH$_2$)c-Pr | SO$_2$(CH$_2$)$_2$OMe | SO$_2$Me | H | |
| 1-471 | SO$_2$Me | F | CF$_3$ | H | |
| 1-472 | SO$_2$Me | NH$_2$ | CF$_3$ | H | |
| 1-473 | SO$_2$Me | NHEt | Cl | H | |
| 1-474 | SMe | SEt | F | H | |
| 1-475 | SMe | SMe | F | H | |
| 1-476 | Me | NH$_2$ | Cl | H | |
| 1-477 | Me | NHMe | Cl | H | |
| 1-478 | Me | NMe$_2$ | Cl | H | |
| 1-479 | Me | pyrazol-1-yl | Cl | H | |
| 1-480 | Me | NH$_2$ | Br | H | |
| 1-481 | Me | NHMe | Br | H | |
| 1-482 | Me | NMe$_2$ | Br | H | |
| 1-483 | Me | NH$_2$ | SO$_2$Me | H | |
| 1-484 | Me | NHMe | SO$_2$Me | H | |
| 1-485 | Me | NMe$_2$ | SO$_2$Me | H | |
| 1-486 | Me | NH(CH$_2$)$_2$OMe | SO$_2$Me | H | |
| 1-487 | Me | morpholin-4-yl | SO$_2$Me | H | |
| 1-488 | Me | 1,2,3-triazol-1-yl | SO$_2$Me | H | |
| 1-489 | Me | 1,2,3-triazol-2-yl | SO$_2$Me | H | 11.85 (s, 1H), 8.89 (d, 1H), 8.54 (s, 1H), 8.13 (d, 1H), 8.05 (s, 1H), 8.03 (d, 1H), 7.06 (s, 1H), 3.13 (s, 3H), 1.88 (s, 3H) |
| 1-490 | Me | pyrazol-1-yl | SO$_2$Me | H | |
| 1-491 | Me | 1,2,4-triazol-1-yl | SO$_2$Me | H | |
| 1-492 | Me | NH$_2$ | CF$_3$ | H | |
| 1-493 | Me | NHMe | CF$_3$ | H | |
| 1-494 | Me | NMe$_2$ | CF$_3$ | H | |
| 1-495 | Me | NH(CH$_2$)$_2$OMe | CF$_3$ | H | |
| 1-496 | Me | morpholin-4-yl | CF$_3$ | H | |
| 1-497 | Me | 1,2,3-triazol-1-yl | CF$_3$ | H | |
| 1-498 | Me | 1,2,3-triazol-2-yl | CF$_3$ | H | |
| 1-499 | Me | pyrazol-1-yl | CF$_3$ | H | |
| 1-500 | Me | 1,2,4-triazol-1-yl | CF$_3$ | H | |
| 1-501 | Cl | NH$_2$ | Cl | H | |
| 1-502 | Cl | NHMe | Cl | H | |
| 1-503 | Cl | NMe$_2$ | Cl | H | |
| 1-504 | Cl | pyrazol-1-yl | Cl | H | |
| 1-505 | Cl | NH$_2$ | Br | H | |
| 1-506 | Cl | NHMe | Br | H | |
| 1-507 | Cl | NMe$_2$ | Br | H | |
| 1-508 | Cl | NH$_2$ | SO$_2$Me | H | |
| 1-509 | Cl | NHMe | SO$_2$Me | H | |
| 1-510 | Cl | NMe$_2$ | SO$_2$Me | H | |
| 1-511 | Cl | NH(CH$_2$)$_2$OMe | SO$_2$Me | H | |
| 1-512 | Cl | morpholin-4-yl | SO$_2$Me | H | |
| 1-513 | Cl | 1,2,3-triazol-1-yl | SO$_2$Me | H | |
| 1-514 | Cl | 1,2,3-triazol-2-yl | SO$_2$Me | H | |
| 1-515 | Cl | pyrazol-1-yl | SO$_2$Me | H | |
| 1-516 | Cl | 1,2,4-triazol-1-yl | SO$_2$Me | H | |
| 1-517 | Cl | NH$_2$ | CF$_3$ | H | |
| 1-518 | Cl | NHMe | CF$_3$ | H | |
| 1-519 | Cl | NMe$_2$ | CF$_3$ | H | |
| 1-520 | Cl | NH(CH$_2$)$_2$OMe | CF$_3$ | H | |

TABLE 1-continued

Compounds of the general formula (I) according to the invention in which R respresents H and A represents C—Y.

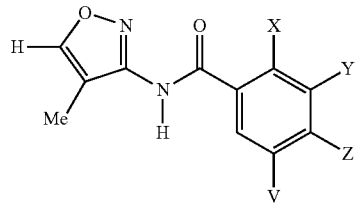

(I)

| No. | X | Y | Z | V | Physical data ($^1$H-NMR, DMSO-$d_6$, 400 MHz) |
|---|---|---|---|---|---|
| 1-521 | Cl | morpholin-4-yl | $CF_3$ | H | |
| 1-522 | Cl | 1,2,3-triazol-1-yl | $CF_3$ | H | |
| 1-523 | Cl | 1,2,3-triazol-2-yl | $CF_3$ | H | |
| 1-524 | Cl | pyrazol-1-yl | $CF_3$ | H | |
| 1-525 | Cl | 1,2,4-triazol-1-yl | $CF_3$ | H | |
| 1-526 | Cl | sulfoximine 1 | Cl | H | |
| 1-527 | Cl | sulfoximine 2 | Cl | H | |
| 1-528 | Cl | sulfoximine 3 | Cl | H | |
| 1-529 | Cl | sulfoximine 4 | Cl | H | |
| 1-530 | Cl | sulfoximine 5 | Cl | H | |
| 1-531 | Cl | sulfoximine 3 | OMe | H | |
| 1-532 | Cl | sulfoximine 4 | OMe | H | |
| 1-533 | Cl | sulfoximine 5 | OMe | H | |
| 1-534 | Cl | sulfoximine 3 | COOMe | H | |
| 1-535 | Cl | sulfoximine 4 | COOMe | H | |
| 1-536 | Cl | sulfoximine 5 | COOMe | H | |
| 1-537 | OMe | sulfoximine 3 | OMe | H | |
| 1-538 | OMe | sulfoximine 4 | OMe | H | |
| 1-539 | OMe | sulfoximine 5 | OMe | H | |
| 1-540 | Me | sulfoximine 1 | $CF_3$ | H | |
| 1-541 | Me | sulfoximine 2 | $CF_3$ | H | |
| 1-542 | Me | sulfoximine 1 | $SO_2Me$ | H | |
| 1-543 | Me | sulfoximine 2 | $SO_2Me$ | H | |
| 1-544 | Me | sulfoximine 1 | Cl | H | |
| 1-545 | Me | sulfoximine 2 | Cl | H | |
| 1-546 | Cl | H | F | F | |

TABLE 2

Compounds of the general formula (I) according to the invention in which R represents methyl, A represents C—Y, and V, X, Y and Z have the meanings given in Table 1.

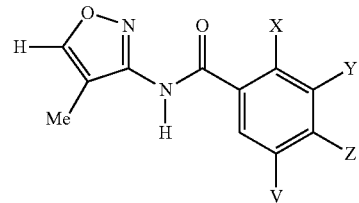

| No. | X | Y | Z | V | Physical data ($^1$H-NMR, DMSO-$d_6$, 400 MHz) |
|---|---|---|---|---|---|
| 2-13 | Cl | H | $SO_2Me$ | H | |
| 2-163 | Me | $SO_2Me$ | $SO_2Me$ | H | 11.01 (s, 1H), 8.71 (s, 1H), 8.25 (d, 1H), 8.03 (d, 1H), 3.60 (s, 3H), 3.56 (s, 3H), 2.72 (s, 3H), 1.99 (s, 3H) |
| 2-172 | Me | SOMe | $CF_3$ | H | 10.98 (s, 1H), 8.70 (s, 1H), 7.85 (d, 1H), 7.82 (d, 1H), 3.05 (s, 3H), 2.87 (s, 3H), 2.01 (s, 3H) |
| 2-173 | Me | $SO_2Me$ | $CF_3$ | H | 11.02 (s, 1H), 8.71 (s, 1H), 8.02 (d, 1H), 7.96 (d, 1H), 3.42 (s, 3H), 2.75 (s, 3H), 2.01 (s, 3H) |
| 2-284 | Cl | SOMe | $SO_2Me$ | H | 11.14 (s, 1H), 8.71 (s, 1H), 8.11 (d, 1H), 8.02 (d, 1H), 3.54 (s, 3H), 3.20 (s, 3H), |

TABLE 2-continued

Compounds of the general formula (I) according to the invention in which R represents methyl, A represents C—Y, and V, X, Y and Z have the meanings given in Table 1.

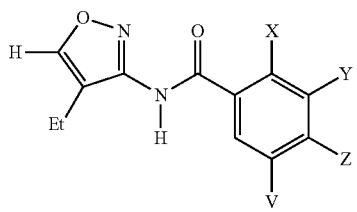

| No. | X | Y | Z | V | Physical data (¹H-NMR, DMSO-$d_6$, 400 MHz) |
|---|---|---|---|---|---|
| 2-285 | Cl | SO₂Me | SO₂Me | H | 2.01 (s, 3H) 11.16 (s, 1H), 8.72 (s, 1H), 8.35 (d, 1H), 8.20 (d, 1H), 3.66 (s, 3H), 3.57 (s, 3H), 2.01 (s, 3H) |
| 2-293 | Cl | SMe | CF₃ | H | 11.06 (s, 1H), 8.71 (s, 1H), 7.93 (d, 1H), 7.84 (d, 1H), 2.45 (s, 3H), 2.02 (s, 3H) |
| 2-294 | Cl | SOMe | CF₃ | H | 11.14 (s, 1H), 8.71 (s, 1H), 8.03 (d, 1H), 7.99 (d, 1H), 3.16 (s, 3H), 2.01 (s, 3H) |
| 2-295 | Cl | SO₂Me | CF₃ | H | 11.18 (s, 1H), 8.72 (s, 1H), 8.16 (d, 1H), 8.14 (d, 1H), 3.53 (s, 3H), 2.02 (s, 3H) |
| 2-328 | Cl | CH₂OMe | SO₂Me | H | 11.09 (s, 1H), 8.71 (s, 1H), 8.08 (d, 1H), 7.88 (d, 1H), 4.98 (s, 1H), 3.42 (s, 3H), 3.36 (s, 3H), 2.00 (s, 3H). |
| 2-334 | Cl | CH₂OCH₂CF₃ | SO₂Me | H | ¹H-NMR, CDCl₃, 400 MHz: 8.56 (bs, 1H), 8.17 (s, 1H), 8.13 (d, 1H), 7.79 (d, 1H), 5.36 (s, 2H), 4.08 (q, 2H), 3.21 (s, 3H), 2.12 (s, 3H). |
| 2-343 | Cl | 5-cyanomethyl-4,5-dihydro-1,2-oxazol-3-yl | SO₂Et | H | 11.18 (s, 1H), 8.74 (s, 1H), 8.12 (d, 1H), 8.05 (d, 1H), 5.19 (m, 1H), 3.60 (dd, 1H), 3.41 (q, 2H), 3.15 (dd, 1H), 3.01 (m, 2H), 2.00 (s, 3H), 1.17 (t, 3H). |
| 2-390 | Me | SMe | CF₃ | H | 10.86 (s, 1H), 8.70 (s, 1H), 7.72 (d, 1H), 7.66 (d, 1H), 3.95 (s, 3H), 2.46 (s, 3H), 2.00 (s, 3H) |

TABLE 3

Compounds of the general formula (I) according to the invention in which R represents ethyl, A represents C—Y, and V, X, Y and Z have the meanings given in Table 1.

TABLE 4

Compounds of the general formula (I) according to the invention in which R represents n-propyl, A represents C—Y, and V, X, Y and Z have the meanings given in Table 1.

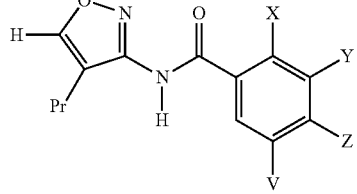

TABLE 5

Compounds of the general formula (I) according to the invention in which R represents isopropyl, A represents C—Y, and V, X, Y and Z have the meanings given in Table 1.

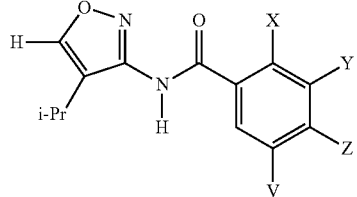

| No. | X | Y | Z | V | Physical data (¹H-NMR, DMSO-$d_6$, 400 MHz) |
|---|---|---|---|---|---|
| 5-163 | Me | SO₂Me | SO₂Me | H | 10.92 (s, 1H), 8.76 (s, 1H), 8.26 (d, 1H), 7.99 (d, 1H), 3.59 (s, 3H), 3.57 (s, 3H), 2.88-2.84 (m, 4H), 2.71 (s, 3H), 1.20 (d, 6H), ), |
| 5-172 | Me | SOMe | CF₃ | H | 10.87 (s, 1H), 8.76 (s, 1H), 7.87 (d, 1H), 7.77 (d, 1H), 3.05 (s, 3H), 2.91-2.84 (m, 4H), 1.20 (d, 6H), ), |
| 5-173 | Me | SO₂Me | CF₃ | H | 10.91 (s, 1H), 8.76 (s, 1H), 8.02 (d, 1H), 7.92 (d, 1H), 3.42 (s, 3H), 2.88-2.83 (m, 1H), 2.75 (s, 3H), 1.20 (d, 6H) |
| 5-343 | Cl | 5-cyanomethyl-4,5-dihydro-1,2-oxazol-3 yl | SO₂Et | H | 11.02 (s, 1H), 8.77 (s, 1H), 8.12 (d, 1H), 8.00 (d, 1H), 5.19 (m, 1H), 3.60 (dd, 1H), 3.41 (q, 2H), 3.18 (dd, 1H), 3.01 (m, 2H), 2.88 (m, 1H), 1.19 (d, 6H). |

TABLE 6

Compounds of the general formula (I) according to the invention in which R represents t-butyl, A represents C—Y, and V, X, Y and Z have the meanings given in Table 1.

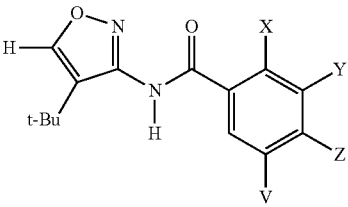

| No. | X | Y | Z | V | Physical data ($^1$H-NMR, DMSO-$d_6$, 400 MHz) |
|---|---|---|---|---|---|
| 6-172 | Me | SOMe | CF$_3$ | H | 10.54 (s, 1H), 8.79 (s, 1H), 7.89 (d, 1H), 7.71 (d, 1H), 2.89 (s, 3H), 1.29 (s, 9H) |
| 6-173 | Me | SO$_2$Me | CF$_3$ | H | 10.58 (s, 1H), 8.79 (s, 1H), 8.04 (d, 1H), 7.84 (d, 1H), 3.41 (s, 3H), 1.279 (s, 9H) |
| 6-343 | Cl | 5-cyanomethyl-4,5-dihydro-1,2-oxazol-3-yl | SO$_2$Et | H | 10.69 (s, 1H), 8.80 (s, 1H), 8.12 (d, 1H), 7.95 (d, 1H), 5.19 (m, 1H), 3.60 (dd, 1H), 3.41 (q, 2H), 3.18 (dd, 1H), 3.01 (m, 2H), 1.30 (s, 9H), 1.15 (t, 3H). |

TABLE 7

Compounds of the general formula (I) according to the invention in which R represents trifluoromethyl, A represents C—Y, and V, X, Y and Z have the meanings given in Table 1.

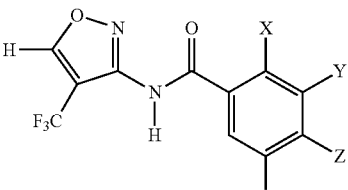

| No. | X | Y | Z | V | Physical data ($^1$H-NMR, DMSO-$d_6$, 400 MHz) |
|---|---|---|---|---|---|
| 7-173 | Me | SO$_2$Me | CF$_3$ | H | 11.48 (s, 1H), 9.85 (s, 1H), 8.04 (d, 1H), 7.90 (d, 1H), 3.43 (s, 3H), 2.73 (s, 3H) |
| 7-293 | Cl | SMe | CF$_3$ | H | 11.49 (s, 1H), 9.83 (s, 1H), 7.94 (d, 1H), 7.76 (d, 1H), 3.32 (s, 3H) |
| 7-294 | Cl | SOMe | CF$_3$ | H | |
| 7-295 | Cl | SOMe | CF$_3$ | H | 11.60 (s, 1H), 9.84 (s, 1H), 8.17 (d, 1H), 8.06 (d, 1H), 3.54 (s, 3H) |
| 7-334 | Cl | CH$_2$OCH$_2$CF$_3$ | SO$_2$Me | H | 11.55 (s, 1H), 9.84 (s, 1H), 8.12 (d, 1H), 7.85 (d, 1H), 5.25 (s, 1H), 4.30 (q, 2H), 3.36 (s, 3H). |

TABLE 8

Compounds of the general formula (I) according to the invention in which R represents chlorine, A represents C—Y, and V, X, Y and Z have the meanings given in Table 1.

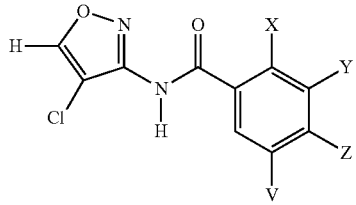

| No. | X | Y | Z | V | Physical data ($^1$H-NMR, DMSO-$d_6$, 400 MHz) |
|---|---|---|---|---|---|
| 8-173 | Me | SO$_2$Me | CF$_3$ | H | 11.30 (s, 1H), 9.35 (s, 1H), 8.03 (d, 1H), 7.95 (d, 1H), 3.43 (s, 3H), 2.76 (s, 3H) |
| 8-293 | Cl | SMe | CF$_3$ | H | 11.31 (s, 1H), 9.34 (s, 1H), 7.93 (d, 1H), 7.82 (d, 1H), 2.44 (s, 3H) |
| 8-334 | Cl | CH$_2$OCH$_2$CF$_3$ | SO$_2$Me | H | 11.38 (s, 1H), 9.34 (s, 1H), 8.11 (d, 1H), 7.91 (d, 1H), 5.25 (s, 1H), 4.29 (q, 2H), 3.37 (s, 3H). |

TABLE 9

Compounds of the general formula (I) according to the invention in which R represents CH$_2$CH$_2$CN, A represents C—Y, and V, X, Y and Z have the meanings given in Table 1.

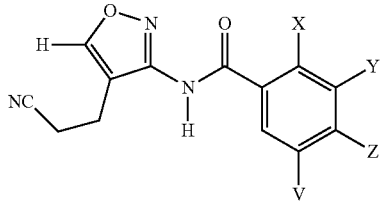

| No. | X | Y | Z | V | Physical data ($^1$H-NMR, DMSO-$d_6$, 400 MHz) |
|---|---|---|---|---|---|
| 9-13 | Cl | H | SO$_2$Me | H | 11.20 (s, 1H), 8.87 (s, 1H), 8.14 (s, 1H), 8.00 (d, 1H), 7.96 (d, 1H), 3.35 (s, 3H), 2.84-2.77 (m, 4H) |
| 9-42 | NO$_2$ | H | SO$_2$Me | H | 11.36 (s, 1H), 8.88 (s, 1H), 8.65 (s, 1H), 8.42 (d, 1H), 8.13 (d, 1H), 3.42 (s, 3H), 2.83-2.80 (m, 4H) |
| 9-111 | Me | NHCH$_2$C(O)-NMe$_2$ | SO$_2$Me | H | 10.90 (s, 1H), 8.85 (s, 1H), 7.64 (d, 1H), 7.27 (d, 1H), 6.30 (t, 1H), 4.05 (d, 1H), 3.20 (s, 3H), 3.31 (s, 3H), 3.42 (s, 3H), 2.82-2.80 (m, 4H) |
| 9-142 | Me | Cl | SO$_2$Me | H | 11.09 (s, 1H), 8.86 (s, 1H), 8.03 (d, 1H), 7.97 (d, 1H), 3.35 (s, 3H), 2.85-2.76 (m, 4H), 2.28 (s, 3H), 2.50 (s, 3H) |
| 9-172 | Me | SOMe | CF$_3$ | H | 11.08 (s, 1H), 8.86 (s, 1H), 7.86 (bs, 2H), 3.05 (s, 3H), 2.86 (s, 3H), 2.85-2.77 (m, 4H) |
| 9-238 | CF$_3$ | F | CF$_3$ | H | 11.33 (s, 1H), 8.88 (s, 1H), 8.29 (t, 1H), 7.88 (d, 1H), 3.31 (s, 3H), 2.84-2.74 (m, 4H), |

TABLE 9-continued

Compounds of the general formula (I) according to the invention in which R represents CH$_2$CH$_2$CN, A represents C—Y, and V, X, Y and Z have the meanings given in Table 1.

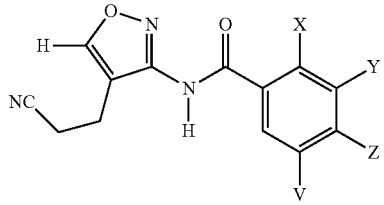

| No. | X | Y | Z | V | Physical data ($^1$H-NMR, DMSO-$d_6$, 400 MHz) |
|---|---|---|---|---|---|
| 9-250 | Cl | Me | SO$_2$Et | H | 11.18 (s, 1H), 8.88 (s, 1H), 8.00 (d, 1H), 7.76 (d, 1H), 3.42 (q, 2H), 2.84-2.78 (m, 4H) |
| 9-324 | Cl | Cl | SO$_2$Me | H | 11.24 (s, 1H), 8.88 (s, 1H), 8.14 (s, 1H), 7.92 (d, 1H), 3.48 (s, 3H), 2.85-2.77 (m, 4H), 2.28 (s, 3H), 1.13 (t, 3H) |
| 9-334 | Cl | CH$_2$OCH$_2$CF$_3$ | SO$_2$Me | H | 11.23 (s, 1H), 8.87 (s, 1H), 7.97 (d, 1H), 7.88 (d, 1H), 5.26 (s, 2H), 4.29 (m, 2H), 3.36 (s, 3H), 2.83-2.80 (m, 4H), |
| 9-343 | Cl | 5-cyanomethyl-4,5-dihydro-1,2-oxazol-3-yl | SO$_2$Et | H | 11.23 (s, 1H), 8.88 (s, 1H), 8.11 (d, 1H), 8.09 (d, 1H), 5.18 (m, 1H), 3.61 (dd, 1H), 3.41 (q, 2H), 3.30 (s, 3H), 3.18 (dd, 1H), 3.01 (m, 2H), 2.81 (m, 4H), 1.15 (t, 3H). |
| 9-348 | Cl | CH$_2$OCH$_2$-tetrahydrofuran-2-yl | SO$_2$Me | H | 11.21 (s, 1H), 8.88 (s, 1H), 8.09 (d, 1H), 7.90 (d, 1H), 5.09 (s, 2H), 3.99-3.94 (m, 1H), 3.74-3.68 (m, 1H), 3.62-3.55 (m, 3H), 3.33 (s, 3H), 2.83-2.79 (m, 4H), 1.92-1.75 (m, 3H), 1.59-1.49 (m, 1H), |

TABLE 10

Compounds of the general formula (I) according to the invention in which A represents N

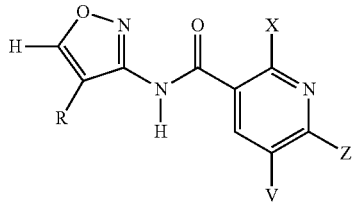

| No. | R | X | Z | V | Physical data ($^1$H-NMR, DMSO-$d_6$, 400 MHz) |
|---|---|---|---|---|---|
| 10-1 | H | Cl | CF$_3$ | H | 10.15 (s, 1H), 8.38 (s, 1H), 8.30 (d, 1H), 7.80 (d, 1H), 7.27 (s, 1H) |
| 10-2 | H | Me | CF$_3$ | H | 11.76 (s, 1H), 8.90 (s, 1H), 8.22 (d, 1H), 7.88 (d, 1H), 7.07 (s, 1H), 2.63 (s, 3H). |

TABLE 10-continued

Compounds of the general formula (I) according to the invention in which A represents N

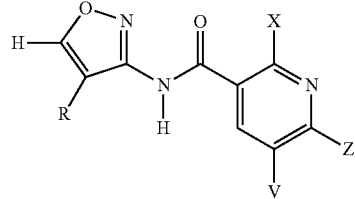

| No. | R | X | Z | V | Physical data ($^1$H-NMR, DMSO-$d_6$, 400 MHz) |
|---|---|---|---|---|---|
| 10-3 | H | CH$_2$OMe | CF$_3$ | H | 11.68 (s, 1H), 8.88 (s, 1H), 8.27 (d, 1H), 8.00 (d, 1H), 7.05 (s, 1H), 4.71 (s, 2H), 3.23 (s, 3H). |
| 10-4 | H | (1,1-dioxido-1,2-thiadiazolidin-1-yl)methyl | CF$_3$ | H | |
| 10-5 | H | CH$_2$OCH$_2$CH$_2$OMe | CF$_3$ | H | |
| 10-6 | H | Cl | Cl | H | |
| 10-7 | Me | Cl | CF$_3$ | H | 11.18 (s, 1H), 8.72 (s, 1H), 8.45 (d, 1H), 8.14 (d, 1H), 2.01 (s, 3H) |
| 10-8 | Me | Me | CF$_3$ | H | |
| 10-9 | Me | CH$_2$OMe | CF$_3$ | H | |
| 10-10 | Me | (1,1-dioxido-1,2-thiadiazolidin-1-yl)methyl | CF$_3$ | H | 11.11 (s, 1H), 8.70 (s, 1H), 8.33 (d, 1H), 8.02 (d, 1H), 4.50 (s, 2H), 3.28 (t, 2H), 3.31 (t, 2H), 2.24-2.20 (m, 2H), 2.00 (s, 3H) |
| 10-11 | Me | CH$_2$OCH$_2$CH$_2$OMe | CF$_3$ | H | |
| 10-12 | Me | | | | |
| 10-13 | Cl | Cl | CF$_3$ | H | |
| 10-14 | Cl | Me | CF$_3$ | H | |
| 10-15 | Cl | CH$_2$OMe | CF$_3$ | H | |
| 10-16 | Cl | (1,1-dioxido-1,2-thiadiazolidin-1-yl)methyl | CF$_3$ | H | |
| 10-17 | Cl | CH$_2$OCH$_2$CH$_2$OMe | CF$_3$ | H | |
| 10-18 | Cl | | | | |
| 10-19 | CF$_3$ | Cl | CF$_3$ | H | |
| 10-20 | CF$_3$ | Me | CF$_3$ | H | |
| 10-21 | CF$_3$ | CH$_2$OMe | CF$_3$ | H | |
| 10-22 | CF$_3$ | (1,1-dioxido-1,2-thiadiazolidin-1-yl)methyl | CF$_3$ | H | |
| 10-23 | CF$_3$ | CH$_2$OCH$_2$CH$_2$OMe | CF$_3$ | H | |
| 10-24 | CF$_3$ | | | | |
| 10-25 | Et | Cl | CF$_3$ | H | |
| 10-26 | Et | Me | CF$_3$ | H | |
| 10-27 | Et | CH$_2$OMe | CF$_3$ | H | |
| 10-28 | Et | (1,1-dioxido-1,2-thiadiazolidin-1-yl)methyl | CF$_3$ | H | |
| 10-29 | Et | CH$_2$OCH$_2$CH$_2$OMe | CF$_3$ | H | |
| 10-30 | Et | | | | |
| 10-31 | n-Pr | Cl | CF$_3$ | H | |
| 10-32 | n-Pr | Me | CF$_3$ | H | |
| 10-33 | n-Pr | CH$_2$OMe | CF$_3$ | H | |
| 10-34 | n-Pr | (1,1-dioxido-1,2-thiadiazolidin-1-yl)methyl | CF$_3$ | H | |
| 10-35 | n-Pr | CH$_2$OCH$_2$CH$_2$OMe | CF$_3$ | H | |
| 10-36 | n-Pr | | | | |
| 10-37 | i-Pr | Cl | CF$_3$ | H | |
| 10-38 | i-Pr | Me | CF$_3$ | H | |
| 10-39 | i-Pr | CH$_2$OMe | CF$_3$ | H | |

TABLE 10-continued

Compounds of the general formula (I) according to the invention in which A represents N

| No. | R | X | Z | V | Physical data ($^1$H-NMR, DMSO-$d_6$, 400 MHz) |
|---|---|---|---|---|---|
| 10-40 | i-Pr | (1,1-dioxido-1,2-thiadiazolidin-1-yl)methyl | $CF_3$ | H | |
| 10-41 | i-Pr | $CH_2OCH_2CH_2OMe$ | $CF_3$ | H | |
| 10-42 | i-Pr | | | | |
| 10-43 | t-Bu | Cl | $CF_3$ | H | |
| 10-44 | t-Bu | Me | $CF_3$ | H | |
| 10-45 | t-Bu | $CH_2OMe$ | $CF_3$ | H | |
| 10-46 | t-Bu | (1,1-dioxido-1,2-thiadiazolidin-1-yl)methyl | $CF_3$ | H | |
| 10-47 | t-Bu | $CH_2OCH_2CH_2OMe$ | $CF_3$ | H | |
| 10-48 | t-Bu | | | | |
| 10-49 | $(CH_2)_2CN$ | Cl | $CF_3$ | H | 11.27 (s, 1H), 8.88 (s, 1H), 8.49 (d, 1H), 8.14 (d, 1H), 7.96 (d, 1H), 3.35 (s, 3H), 2.83-2.80 (m, 4H) |
| 10-50 | $(CH_2)_2CN$ | Me | $CF_3$ | H | |
| 10-51 | $(CH_2)_2CN$ | $CH_2OMe$ | $CF_3$ | H | |
| 10-52 | $(CH_2)_2CN$ | (1,1-dioxido-1,2-thiadiazolidin-1-yl)methyl | $CF_3$ | H | |
| 10-53 | $(CH_2)_2CN$ | $CH_2OCH_2CH_2OMe$ | $CF_3$ | H | |

B. FORMULATION EXAMPLES a) A dusting product is obtained by mixing 10 parts by weight of a compound of the formula (I) and/or salts thereof and 90 parts by weight of talc as an inert substance and comminuting the mixture in a hammer mill.

b) A readily water-dispersible wettable powder is obtained by mixing 25 parts by weight of a compound of the formula (I) and/or salts thereof, 64 parts by weight of kaolin-containing quartz as an inert substance, 10 parts by weight of potassium lignosulfonate and 1 part by weight of sodium oleoylmethyltaurate as a wetting agent and dispersant, and grinding the mixture in a pinned-disk mill.

c) A readily water-dispersible dispersion concentrate is obtained by mixing 20 parts by weight of a compound of the formula (I) and/or salts thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.) and grinding the mixture in a friction ball mill to a fineness of below 5 microns.

d) An emulsifiable concentrate is obtained from 15 parts by weight of a compound of the formula (I) and/or salts thereof, 75 parts by weight of cyclohexanone as a solvent and 10 parts by weight of ethoxylated nonylphenol as an emulsifier.

e) Water-dispersible granules are obtained by mixing
   75 parts by weight of a compound of the formula (I) and/or salts thereof,
   10 parts by weight of calcium lignosulfonate,
   5 parts by weight of sodium laurylsulfate,
   3 parts by weight of polyvinyl alcohol and
   7 parts by weight of kaolin,
   grinding the mixture in a pinned-disk mill, and granulating the powder in a fluidized bed by spray application of water as a granulating liquid.

f) Water-dispersible granules are also obtained by homogenizing and precomminuting, in a colloid mill,
   25 parts by weight of a compound of the formula (I) and/or salts thereof,
   5 parts by weight of sodium 2,2'-dinaphthylmethane-6,6'-disulfonate,
   2 parts by weight of sodium oleoylmethyltaurate,
   1 part by weight of polyvinyl alcohol,
   17 parts by weight of calcium carbonate and
   50 parts by weight of water,
   then grinding the mixture in a bead mill and atomizing and drying the suspension thus obtained in a spray tower by means of a one-phase nozzle.

C. BIOLOGICAL EXAMPLES

1. Pre-Emergence Herbicidal Action Against Harmful Plants

Seeds of monocotyledonous and dicotyledonous weed plants and crop plants are laid out in wood-fiber pots in sandy loam and covered with soil. The compounds according to the invention, formulated in the form of wettable powders (WP) or as emulsion concentrates (EC), are then applied to the surface of the soil cover in the form of an aqueous suspension or emulsion at a water application rate equating to 600 to 800 l/ha, with addition of 0.2% wetting agent. After the treatment, the pots are placed in a greenhouse and kept under good growth conditions for the test plants. The damage to the test plants is assessed visually after a test period of 3 weeks by comparison with untreated controls (herbicidal activity in percent (%): 100% activity=the plants have died, 0% activity=like control plants). Here, for example, compounds No. 1-173, 1-284, 1-293, 1-294, 1-295, 2-163, 2-173, 2-293, 2-295, 5-163 and 5-343, at an application rate of 320 g/ha, have an activity of at least 80% against *Abutilon theophrasti*, *Amaranthus retroflexus* and *Veronica persica*.

2. Post-Emergence Herbicidal Action Against Harmful Plants

Seeds of monocotyledonous and dicotyledonous weed plants and crop plants are laid out in wood fiber pots in sandy loam, covered with soil and cultivated in a greenhouse under good growth conditions. 2 to 3 weeks after sowing, the test plants are treated at the one-leaf stage. The compounds according to the invention, formulated in the form of wettable powders (WP) or as emulsion concentrates (EC), are then sprayed onto the green parts of the plants in the form of an aqueous suspension or emulsion at a water application rate equating to 600 to 800 l/ha, with addition of 0.2% wetting agent. After the test plants have been left to stand in the greenhouse under optimal growth conditions for about 3 weeks, the action of the preparations is assessed visually in comparison to untreated controls (herbicidal action in percent (%): 100% activity=the plants have died, 0% activity=like control plants). Here, for example, compounds No. 1-173, 1-284, 1-294, 1-295, 2-163, 2-294, 2-295, 5-172, 5-343 and 9-343, at an application rate of 80 g/ha, have an activity of at least 80% against *Abutilon theophrasti*.

The invention claimed is:

1. The N-(isoxazol-3-yl)arylcarboxamide and/or salt of formula (1)

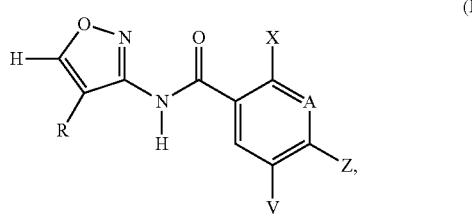

in which
A represents CY,
X represents nitro, halogen, cyano, $(C_1-C_6)$-alkyl, halo-$(C_1-C_6)$-alkyl, $(C_3-C_6)$-cycloalkyl, $OR^2$, $S(O)_nR^2$, $(C_1-C_6)$-alkyl-$S(O)_nR^2$, $(C_1-C_6)$-alkyl-$OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, or $(C_1-C_6)$-alkyl-$NR^1SO_2R^2$,
Y represents $S(O)_nR^2$,
Z represents halogen, cyano, nitro, $(C_1-C_6)$-alkyl, $(C_1-C_6)$-alkoxy, halo-$(C_1-C_6)$-alkyl, $(C_3-C_6)$-cycloalkyl, $S(O)_nR^2$, or hydrogen,
V represents hydrogen, $(C_1-C_6)$-alkyl, halo-$(C_1-C_6)$-alkyl, $(C_1-C_6)$-alkoxy, $(C_1-C_6)$-halo-alkoxy, $S(O)_n$—$(C_1-C_6)$-alkyl, $S(O)_n$—$(C_1-C_6)$-haloalkyl, $(C_1-C_6)$-alkoxy-$(C_1-C_4)$-alkyl, halogen, nitro or cyano,
R represents hydrogen, $(C_1-C_6)$-alkyl, $(C_3-C_7)$-cycloalkyl, halo-$(C_1-C_6)$-alkyl, $(C_1-C_6)$-alkoxy, halo-$(C_1-C_6)$-alkoxy, cyano-$(C_1-C_6)$-alkyl, cyano, methylsulfenyl, methyl-sulfinyl, methylsulfonyl, acetylamino, halogen, amino, or methoxymethyl,
$R^1$ represents hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, phenyl, phenyl-$(C_1-C_6)$-alkyl, where the 8 last-mentioned radicals are substituted by s radicals selected from the group consisting of cyano, halogen, nitro, $OR^3$, $S(O)_nR^4$, $N(R^3)_2$, $NR^3OR^3$, $COR^3$, $OCOR^3$, $NR^3COR^3$, $NR^3SO_2R^4$, $CO_2R^3$, $CON(R^3)_2$ and $(C_1-C_4)$-alkoxy-$(C_2-C_6)$-alkoxycarbonyl,
$R^2$ represents $(C_1-C_6)$-alkyl, $(C_3-C_6)$-cycloalkyl or $(C_3-C_6)$-cycloalkyl-$(C_1-C_6)$-alkyl that are each substituted by s radicals selected from the group consisting of halogen and $OR^3$,
$R^3$ represents hydrogen or $(C_1-C_6)$-alkyl,
$R^4$ represents $(C_1-C_6)$-alkyl,
n represents 1 or 2, and
s represents 0, 1, 2 or 3.

2. A herbicidal composition comprising a herbicidally active content of at least one compound of formula (I) as claimed in claim 1 and one more formulation auxiliaries.

3. A method for controlling unwanted plants, comprising applying an effective amount of at least one compound of formula (I) as claimed in claim 1 to the plants and/or to a site of the unwanted plants.

4. A method as claimed in claim 3, wherein the compound of formula (I) controls one or more unwanted plants in crops of useful plants.

5. A method as claimed in claim 4, wherein the useful plants are transgenic useful plants.

6. An N-(isoxazol-3-yl)arylcarboxamide of formula (I) and/or a salt thereof as claimed in claim 1, wherein R is other than hydrogen.

7. An N-(isoxazol-3-yl)arylcarboxamide of formula (I) and/or a salt thereof as claimed in claim 1, wherein Z represents cyano, nitro, $(C_1-C_6)$-alkyl, halo-$(C_1-C_6)$-alkyl, $(C_3-C_6)$-cycloalkyl, $S(O)_nR^2$, or hydrogen.

8. An N-(isoxazol-3-yl)arylcarboxamide of formula (I) and/or a salt thereof as claimed in claim 1, wherein X represents cyano, $(C_1-C_6)$-alkyl, halo-$(C_1-C_6)$-alkyl, $(C_3-C_6)$-cycloalkyl, $OR^2$, $S(O)_nR^2$, $(C_1-C_6)$-alkyl-$S(O)_nR^2$, $(C_1-C_6)$-alkyl-$OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, or $(C_1-C_6)$-alkyl-$NR^1SO_2R^2$.

9. An N-(isoxazol-3-yl)arylcarboxamide of formula (I) and/or a salt thereof as claimed in claim 1, wherein R represents $(C_3-C_7)$-cycloalkyl, halo-$(C_1-C_6)$-alkyl, $(C_1-C_6)$-alkoxy, halo-$(C_1-C_6)$-alkoxy, cyano-$(C_1-C_6)$-alkyl, cyano, methylsulfenyl, methyl-sulfinyl, methylsulfonyl, acetylamino, halogen, amino, or methoxymethyl.

10. An N-(isoxazol-3-yl)arylcarboxamide of formula (I) and/or a salt thereof as claimed in claim 1, wherein R represents $(C_1-C_6)$-alkyl.

11. An N-(isoxazol-3-yl)arylcarboxamide of formula (I) and/or a salt thereof as claimed in claim 1, wherein
A represents CY,
X represents nitro, halogen, cyano, $(C_1-C_6)$-alkyl, halo-$(C_1-C_6)$-alkyl, $(C_3-C_6)$-cycloalkyl, $OR^2$, $S(O)_nR^2$, $(C_1-C_6)$-alkyl-$S(O)_nR^2$, or $(C_1-C_6)$-alkyl-$OR^1$,
Y $S(O)_nR^2$,
Z represents halogen, cyano, nitro, $(C_1-C_6)$-alkyl, $(C_1-C_6)$-alkoxy, halo-$(C_1-C_6)$-alkyl, or $S(O)_nR^2$, or Z optionally represents hydrogen if Y represents $S(O)_nR^2$,
V represents hydrogen,
R represents hydrogen, $(C_1-C_6)$-alkyl, (halo-$(C_1-C_6)$-alkyl, $(C_1-C_6)$-alkoxy, halo-$(C_1-C_6)$-alkoxy, cyano-$(C_1-C_6)$-alkyl, cyano, or halogen,
$R^1$ represents hydrogen, $(C_1-C_6)$-alkyl, $(C_3-C_6)$-cycloalkyl, $(C_1-C_6)$-alkyl-O—$(C_1-C_6)$-alkyl, where the 3 last-mentioned radicals are substituted by s radicals selected from the group consisting of cyano, halogen, and $OR^3$,
$R^2$ represents $(C_1-C_6)$-alkyl that is substituted by s radicals selected from the group consisting of halogen and $OR^3$,
$R^3$ represents hydrogen or $(C_1-C_6)$-alkyl,
$R^4$ represents $(C_1-C_6)$-alkyl,
n represents 1 or 2, and
s represents 0 or 1.

12. An N-(isoxazol-3-yl)arylcarboxamide of formula (I) and/or a salt thereof as claimed in claim 1, wherein
A represents CY,
X represents $(C_1-C_6)$-alkyl,
Y $S(O)_nR^2$,
Z represents halo-$(C_1-C_6)$-alkyl or $S(O)_nR^2$,
V represents hydrogen,
R represents hydrogen, $(C_1-C_6)$-alkyl, or halogen,
$R^2$ represents $(C_1-C_6)$-alkyl,
n represents 1 or 2, and
s represents 0.

* * * * *